(12) United States Patent
Crump et al.

(10) Patent No.: US 6,543,451 B1
(45) Date of Patent: *Apr. 8, 2003

(54) ENDOTRACHEAL CATHETER AND MANIFOLD ASSEMBLY WITH IMPROVED SEAL AND VALVE

(75) Inventors: Chet M. Crump, Draper, UT (US); Edward B. Madsen, Riverton, UT (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 09/471,317

(22) Filed: Dec. 23, 1999

(51) Int. Cl.[7] .............................................. A61M 16/00

(52) U.S. Cl. .............................. 128/207.14; 128/207.16

(58) Field of Search ...................... 128/207.14–207.16, 128/910, 911, 912; 604/35

(56) References Cited

U.S. PATENT DOCUMENTS

| | | |
|---|---|---|
| 3,831,629 A | 8/1974 | Mackal et al. |
| 3,834,388 A | 9/1974 | Sauer |
| 3,902,500 A | 9/1975 | Dryden |
| 3,937,220 A | 2/1976 | Coyne |
| 3,991,762 A | 11/1976 | Radford |
| 4,015,336 A | 4/1977 | Johnson |
| 4,047,527 A | 9/1977 | Kelsen |
| 4,193,406 A | 3/1980 | Jinotti |
| 4,351,328 A | 9/1982 | Bodai |
| 4,468,224 A | 8/1984 | Enzmann et al. |
| 4,510,933 A | 4/1985 | Wendt et al. |
| 4,516,573 A | 5/1985 | Gedeon |
| 4,569,344 A | 2/1986 | Palmer |
| 4,573,965 A | 3/1986 | Russo |
| 4,573,979 A | 3/1986 | Blake |
| 4,574,173 A | 3/1986 | Bennett |
| 4,595,005 A | 6/1986 | Jinotti |
| 4,638,539 A | 1/1987 | Palmer |
| 4,649,913 A | 3/1987 | Watson |
| 4,657,008 A | 4/1987 | Broddner et al. |
| 4,696,305 A | 9/1987 | von Berg |
| 4,705,073 A | 11/1987 | Beck |
| 4,834,726 A | 5/1989 | Lambert |
| 4,909,248 A | 3/1990 | McLennan Anderson |
| 4,929,426 A | 5/1990 | Bodai et al. |
| 4,967,743 A | 11/1990 | Lambert |
| D312,880 S | 12/1990 | Bodai et al. |
| 5,060,646 A | 10/1991 | Page |

(List continued on next page.)

FOREIGN PATENT DOCUMENTS

| | | |
|---|---|---|
| FR | 2528707 | 12/1983 |
| GB | 810517 A | 5/1959 |
| GB | 2199630 A | 7/1988 |
| WO | WO 9630069 | 10/1996 |

*Primary Examiner*—Weilun Lo
*Assistant Examiner*—Teena Mitchell
(74) *Attorney, Agent, or Firm*—William W. Letson; John Wilson Jones

(57) ABSTRACT

An improved respiratory suction apparatus catheter comprising a manifold for attachment to the distal hub of an endotracheal tube to form a ventilation circuit, a catheter tube which is displaceable through the manifold and into the endotracheal tube to suction secretions from the tube and lungs, and at least one wiper seal disposed adjacent the ventilation circuit to minimize the draw of air from the ventilation circuit of a patient while the catheter is being cleaned. In a preferred embodiment of the invention, the catheter is cleaned more thoroughly than in the prior art while simultaneously drawing little or no air from the patient's ventilation circuit, thus extending the usable duration of the catheter apparatus. Another preferred embodiment comprises a valve, most preferably a flap valve distal of the wiper seal within the manifold, improves the cleaning of the catheter by selectively restricting or occluding the retracted catheter.

26 Claims, 20 Drawing Sheets

U.S. PATENT DOCUMENTS

| | | | |
|---|---|---|---|
| 5,073,164 A | 12/1991 | Hollister et al. | |
| 5,083,561 A | 1/1992 | Russo | |
| 5,088,486 A | 2/1992 | Jinotti | |
| 5,107,829 A | 4/1992 | Lambert | |
| 5,125,893 A | 6/1992 | Dryden | |
| 5,134,996 A | 8/1992 | Bell | |
| 5,139,018 A | 8/1992 | Brodsky et al. | |
| 5,140,983 A | 8/1992 | Jinotti | |
| 5,158,569 A | 10/1992 | Strickland et al. | |
| 5,184,611 A | 2/1993 | Turnbull | |
| 5,191,881 A | 3/1993 | Beck | |
| 5,213,096 A | 5/1993 | Kihlberg et al. | |
| 5,215,522 A | 6/1993 | Page et al. | |
| 5,230,332 A | 7/1993 | Strickland | |
| 5,242,084 A | 9/1993 | Jinotti | |
| 5,254,098 A | 10/1993 | Ulrich et al. | |
| 5,255,676 A | 10/1993 | Russo | |
| 5,277,177 A | 1/1994 | Page et al. | |
| 5,300,043 A | 4/1994 | Devlin et al. | |
| 5,309,902 A | 5/1994 | Kee et al. | |
| 5,309,904 A | 5/1994 | Beck | |
| 5,325,850 A | 7/1994 | Ulrich et al. | |
| 5,325,851 A | 7/1994 | Reynolds et al. | |
| 5,333,606 A | 8/1994 | Schneider et al. | |
| 5,333,607 A | 8/1994 | Kee et al. | |
| 5,337,780 A | 8/1994 | Kee | |
| 5,343,857 A | 9/1994 | Schneider et al. | |
| 5,346,478 A | 9/1994 | Jinotti | |
| 5,349,950 A | 9/1994 | Ulrich et al. | |
| 5,354,267 A | 10/1994 | Niermann et al. | |
| 5,355,876 A | 10/1994 | Brodsky et al. | |
| 5,357,946 A | 10/1994 | Kee et al. | |
| 5,368,017 A | 11/1994 | Sorenson et al. | |
| 5,370,610 A | 12/1994 | Reynolds | |
| 5,445,141 A | 8/1995 | Kee et al. | |
| 5,449,348 A | 9/1995 | Dryden | |
| 5,460,613 A | 10/1995 | Ulrich et al. | |
| 5,487,381 A | 1/1996 | Jinotti | |
| 5,490,503 A | 2/1996 | Hollister | |
| 5,496,287 A | 3/1996 | Jinotti | |
| 5,513,627 A | 5/1996 | Flam | |
| 5,513,628 A | 5/1996 | Coles et al. | |
| 5,578,006 A | 11/1996 | Schön | |
| 5,582,161 A | 12/1996 | Kee | |
| 5,582,165 A | 12/1996 | Bryan et al. | |
| 5,598,840 A | 2/1997 | Iund et al. | |
| 5,605,149 A | 2/1997 | Warters | |
| 5,628,306 A | 5/1997 | Kee | |
| 5,642,726 A | 7/1997 | Owens et al. | |
| 5,664,594 A | 9/1997 | Kee | |
| 5,676,136 A | 10/1997 | Russo | |
| 5,738,091 A | 4/1998 | Kee et al. | |
| 5,769,702 A | 6/1998 | Hanson | |
| 5,775,325 A | 7/1998 | Russo | |
| 5,791,337 A | 8/1998 | Coles et al. | |
| 5,813,402 A | 9/1998 | Jinotti | |
| 5,855,562 A | 1/1999 | Moore et al. | |
| 5,882,348 A | 3/1999 | Winterton et al. | |
| 5,919,174 A | 7/1999 | Hanson | |
| 6,070,582 A * | 6/2000 | Kee | 128/207.16 |
| 6,168,758 B1 * | 1/2001 | Forsberg et al. | 422/61 |
| 6,227,200 B1 * | 5/2001 | Crump et al. | 128/207.16 |

* cited by examiner

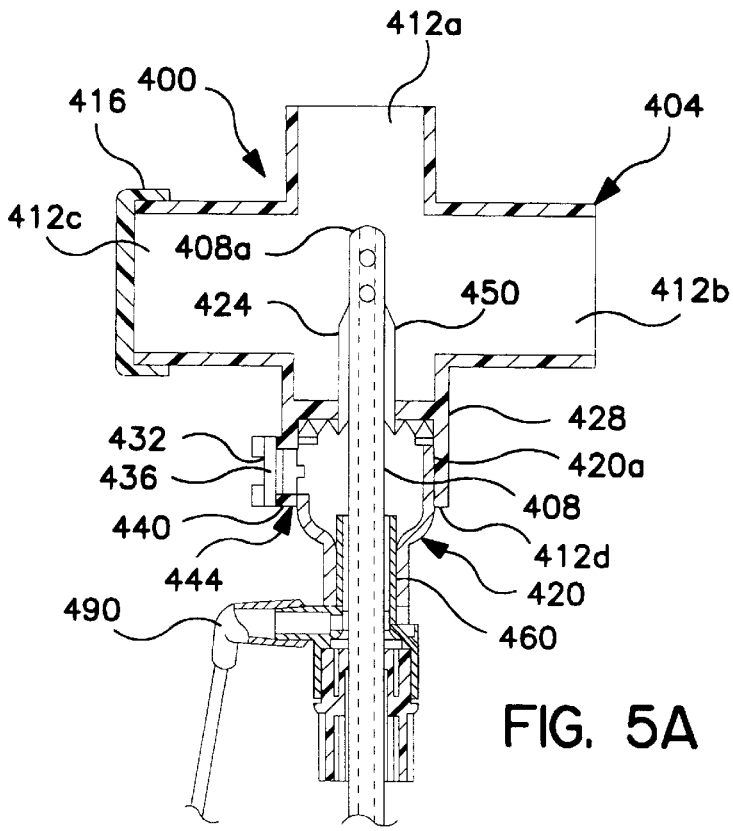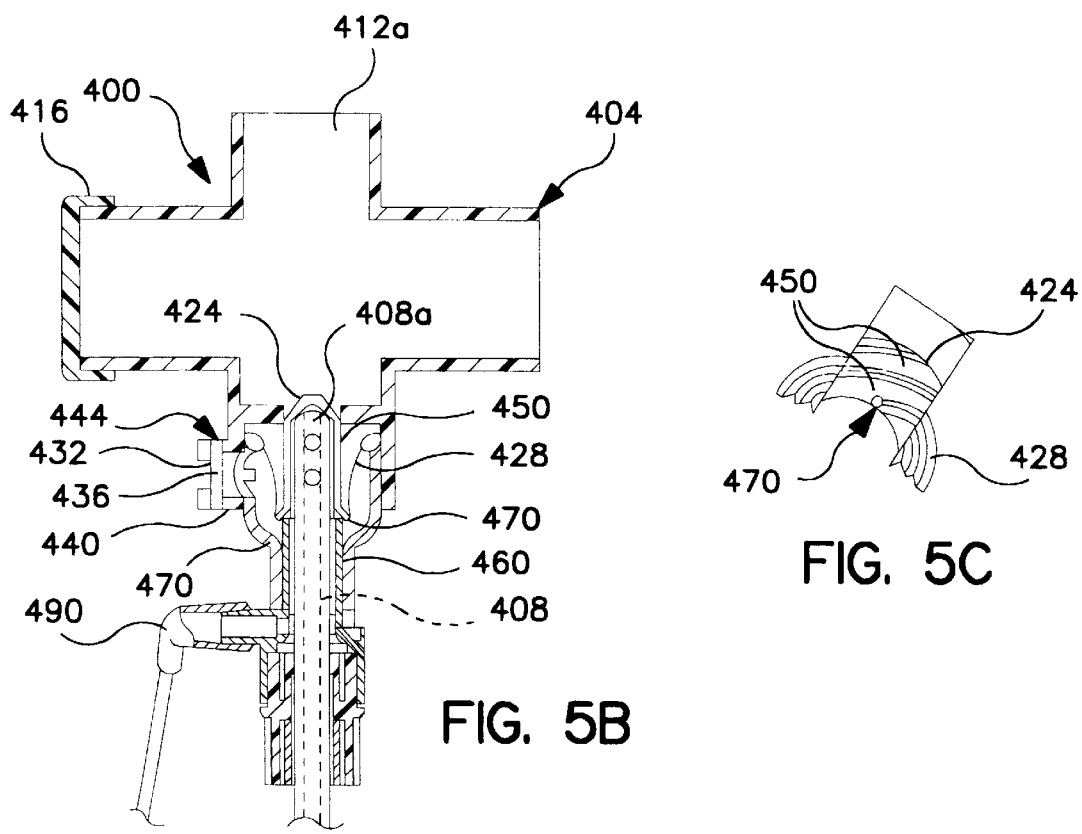
FIG. 5A
FIG. 5B
FIG. 5C

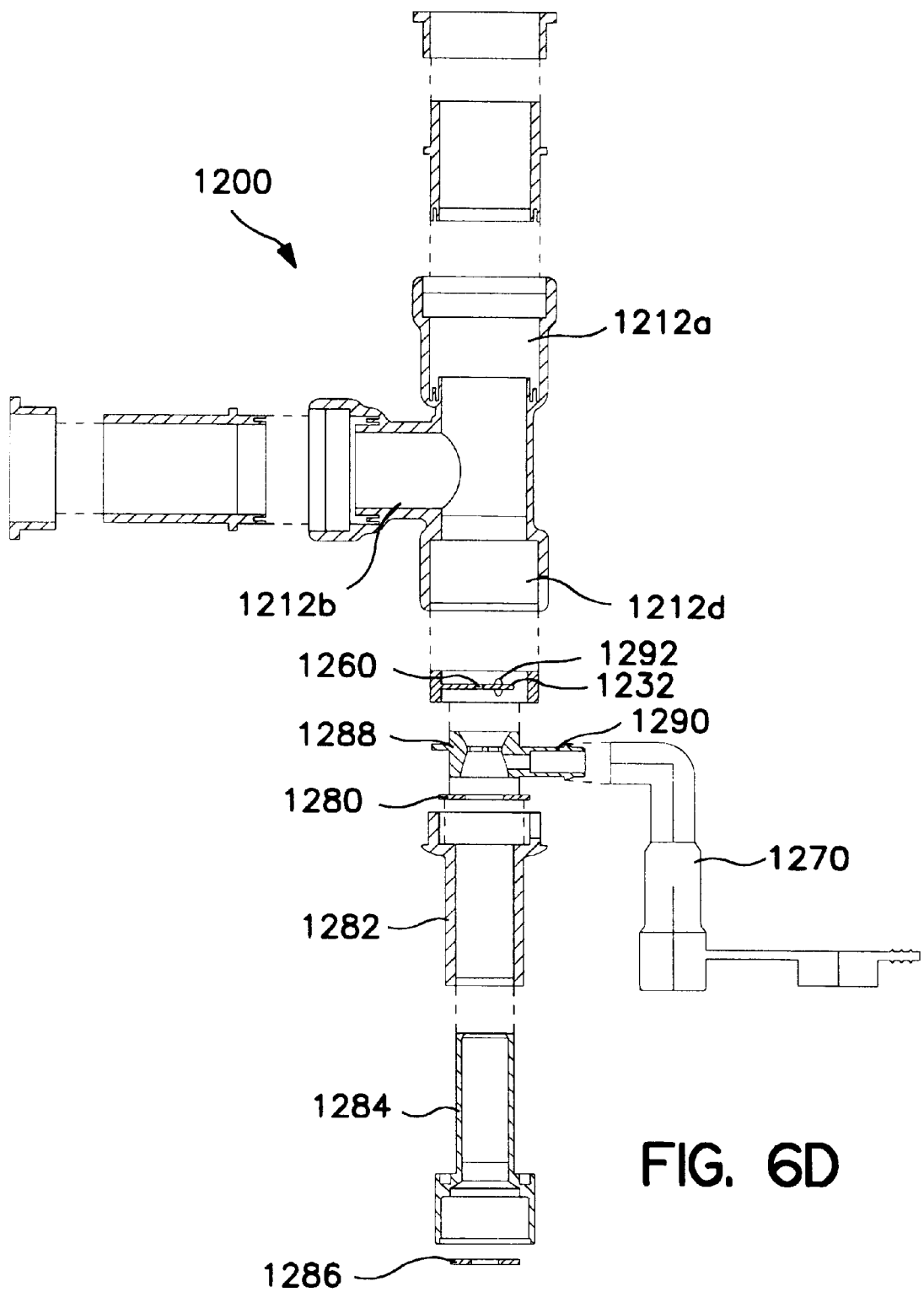

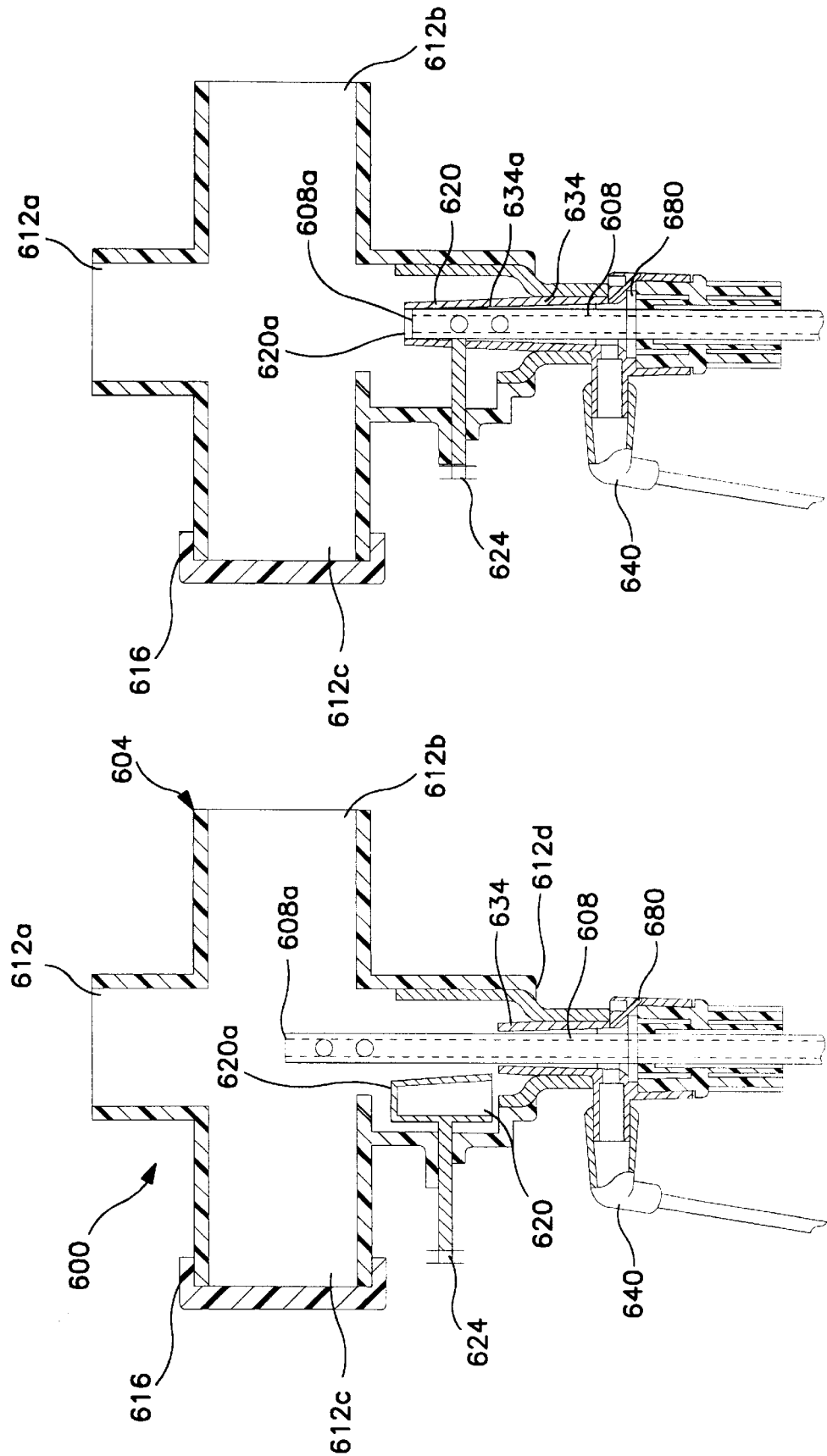

ENDOTRACHEAL CATHETER AND MANIFOLD ASSEMBLY WITH IMPROVED SEAL AND VALVE

FIELD OF THE INVENTION

The present invention relates to a respiratory suction catheter assembly with an improved mechanism for cleaning the tip of the catheter without drawing an excessive amount of air from the respiration circuit to which the endotracheal catheter is attached. More specifically, the present invention relates principally to a closed suction endotracheal catheter system that provides improved cleaning of the catheter by incorporating a wiper seal and valve arrangement that isolates the distal end of the catheter during cleaning while minimizing or eliminating air drawn from the patient's ventilation circuit.

BACKGROUND OF THE INVENTION

There are a variety of different circumstances under which a person may be required to have an artificial airway, such as an endotracheal tube, placed in his or her respiratory system. In some circumstances, such as surgery, the artificial airway's function is primarily to keep the patient's airway open so that adequate lung ventilation can be maintained during the procedure. In many other situations, however, the endotracheal tube will be left in the patient for a prolonged period of time. For example, with many patients, the endotracheal tube will remain in place to sustain mechanical ventilation for the life of the patient.

If an endotracheal tube is to be left in place for any substantial amount of time, it is critical that respiratory secretions be periodically removed. This is most often accomplished with the use of a respiratory suction catheter that is advanced into the endotracheal tube. As the suction catheter is withdrawn, a negative pressure is applied to the interior of the catheter to draw mucus and other secretions from the patient's respiratory system. While a substantial amount of the mucus and other secretions will be withdrawn through the catheter, a portion of the mucus and other secretions remain on the outside of the catheter.

Because a patient's secretions can contain infectious agents, such as streptococcus, pseudomonus, staphylococcus, and even HIV, it is important to shield clinicians from contact with the catheter. Likewise, it is important to shield patients from communicable pathogens in the environment and those that may be carried by the clinician. This is particularly important because patients on mechanical ventilation often have compromised immune systems.

In addition to concerns of cross-contamination, suctioning a patient's artificial airway potentially interferes with proper respiration. The most common group of patients who have indwelling endotracheal tubes for prolonged periods are those who must be mechanically ventilated. Mechanically ventilated patients will typically have a fitting or manifold attached to the proximal end of the endotracheal tube (i.e., the end extending outside the patient) at an endotracheal tube hub. A pair of ventilator tubes extends from a mechanical ventilator and is typically attached to the manifold by an adapter. One tube provides inspiratory air to the patient for inhalation. The other tube allows for exhaled or expiratory air to exit the system.

Until the 1980s, it was common to disconnect the patient from the manifold and ventilator tubes each time the patient needed to be suctioned. Interference with the air supply to the patient, even if only for a few seconds, was often unnecessarily distressing to the patient. These problems were initially overcome in the invention disclosed in U.S. Pat. No. 3,991,762. The '762 patent developed what is commonly referred to as a closed suction catheter system. In a closed suction catheter system, the catheter is maintained within a protective sleeve that is attached to the manifold. When suctioning is desired, the catheter is advanced through the manifold and into the artificial airway. Negative pressure is then applied to the catheter and secretions within the patient's respiratory system are evacuated.

Improvements were made to the system by the invention disclosed in U.S. Pat. No. 4,569,344. This system reduces the risk of cross-contamination between the patient and the medical personnel using the device.

In the last fifteen years, there has been a significant shift toward the use of closed suction catheter systems. The advantage of closed suction catheters is that the ventilating circuit is not detached from the patient during suction procedures, as it is during open suction procedures. Because the catheter is reused a number of times over a twenty-four hour period, it is important that mucus and other secretions are cleaned from the catheter prior to periods of non-use. If the secretions are not removed the risk of auto-contamination increases. It is also important to clean the catheter to maintain suction efficiency.

There are several mechanisms by which the catheter may be cleaned. U.S. Pat. No. 4,569,344 discloses a lavage port which enables the user to inject liquid into the area surrounding the distal end of the catheter after it has been withdrawn from the patient. When liquid is injected into the closed suction catheter apparatus and suction is applied, the liquid aids in loosening and removing the secretions from the exterior of the catheter.

Unfortunately, the suction also causes an undesired amount of respiratory air to be removed through the catheter. In a "closed system," the air that is evacuated potentially disrupts the carefully controlled ventilatory cycles. Thus, the amount of respiratory air available to the patient is potentially decreased as a result of catheter cleaning. If the clinician has a difficult time cleaning secretions from the catheter, suction may be applied through the catheter several times—thereby repeatedly drawing air from the ventilatory circuit.

Other closed suction, catheters have been developed to have a cleaning or lavage chamber that is physically isolated from the ventilation circuit. For example, U.S. Pat. No. 5,487,381 discloses a closed suction catheter which has a lavage chamber configured to receive the distal tip of the catheter as it is withdrawn from the manifold. A wall is then slid from an open position to a closed position to isolate the distal end of the catheter from the manifold and the ventilation circuit. A port is commonly provided to inject lavage solution into the cleaning chamber. Unfortunately, such closed suction catheters may fail to permit adequate airflow, thereby resulting in insufficient cleansing of the suction catheter. The application of negative pressure in the catheter further creates a vacuum within the chamber in the absence of sufficient airflow into the chamber. As a result, the isolated chamber inhibits free evacuation of the cleaning solution. Retention of the cleansing composition further increases the likelihood of reintroducing into the patient contaminated liquids once the chamber is opened.

In addition to the above concerns, the clinician, using commercially available closed suction catheters, is unable to adequately clean the catheter tip. If pathogens or other contaminants remain on the catheter for an extended period of time, there is increased risk of contaminating the patient. Additionally should the catheter become dried with mucus and other secretions, suction efficiency is hampered. Further, premature replacement of the closed suction catheter apparatus often occurs in light of the unsightly appearance of the dried catheters containing mucus. Thus, the need exists for a catheter apparatus capable of more effectively cleansing the distal end of the catheter without creating a substantial draw on respiratory air in the ventilation circuit.

SUMMARY OF THE INVENTION

The present invention relates to an improved respiratory suction catheter apparatus that contains a manifold and a suction catheter for use in attachment an endotracheal tube. In use, the manifold is attached to an artificial airway to form a ventilation circuit. The catheter is displaceable through the manifold and into the patient for the suctioning of secretions from the lungs. At least one seal capable of wiping a distal tip of the catheter is disposed within the manifold. This seal permits the cleansing of the catheter as the catheter is retracted from the patient and exits the manifold. The seal further minimizes the amount of air drawn from the ventilation circuit while the catheter is being cleaned. As a result, the respiratory suction catheter apparatus of the invention accomplishes the removal of mucus and other secretions from the distal tip of the catheter.

The embodiments of an improved respiratory suction catheter apparatus typically include a manifold for attachment to an artificial airway, such as an endotracheal tube, to form a ventilation circuit, a catheter which is displaceable through the manifold and into the artificial airway to suction secretions from the artificial airway and lungs, and a wiper seal and valve configuration disposed adjacent the ventilation circuit to minimize the air drawn from the ventilation circuit of a patient while the catheter is being cleaned.

In a preferred embodiment, the valve is configured to automatically engage the catheter tip after it is withdrawn through the manifold, thereby minimizing the amount of air drawn into the catheter during cleaning. Moreover, the valve may be configured to lock in a closed position when it is pulled toward the withdrawn catheter, thereby ensuring isolation of the catheter tip from the manifold.

BRIEF DESCRIPTION OF THE DRAWINGS

The above and other objects, features and advantages of the invention will become apparent from a consideration of the following detailed description presented in connection with the accompanying drawings in which:

FIG. 4C shows a fragmented, cross-sectional view of the embodiment of FIGS. 4A and 4B, with an air makeup mechanism in an open position to facilitate suctioning of mucus and the like;

FIG. 5A shows a fragmented, cross-sectional view of an alternative embodiment of an improved respiratory suction catheter apparatus having a valve in an open position in accordance with the principles of the present invention;

FIG. 5B shows a fragmented, cross-sectional view of the embodiment shown in FIG. 5A with the valve in a closed position;

FIG. 5C shows a partial cross-sectional view of the valve of the embodiment shown in FIGS. 5A and 5B;

FIG. 6D is an exploded, partial, cross-sectional view of an improved respiratory suction catheter apparatus comprising a seal for wiping contaminants from the distal end of the catheter and an alternative embodiment for a valve;

FIG. 8A shows a fragmented, cross-sectional view of still yet another embodiment of an improved respiratory suction catheter apparatus made in accordance with the principles of the present invention;

FIG. 8B shows a fragmented, cross-section view of the improved endotracheal catheter of FIG. 8A, wherein the valve mechanism is in a closed configuration;

DESCRIPTION OF THE PREFERRED EMBODIMENTS

Reference will now be made to the drawings in which the various elements of the present invention will be given numeral designations wherein like numerals are used to designate like materials throughout. These numeral designations associate the various aspects of these preferred embodiments and are not intended to restrict the scope of the invention as disclosed and claimed herein. It is to be understood that the following description is only exemplary of the principles of the present invention, and should not be viewed as narrowing the pending claims. Those skilled in the art will appreciate that aspects of the various embodiments discussed may be interchanged and modified without departing from the scope and spirit of the invention. Moreover, the use of different numeral designations with corresponding elements within subsequent Figures is merely for clarity and not designed to constrain the scope of the invention.

Figure 1:
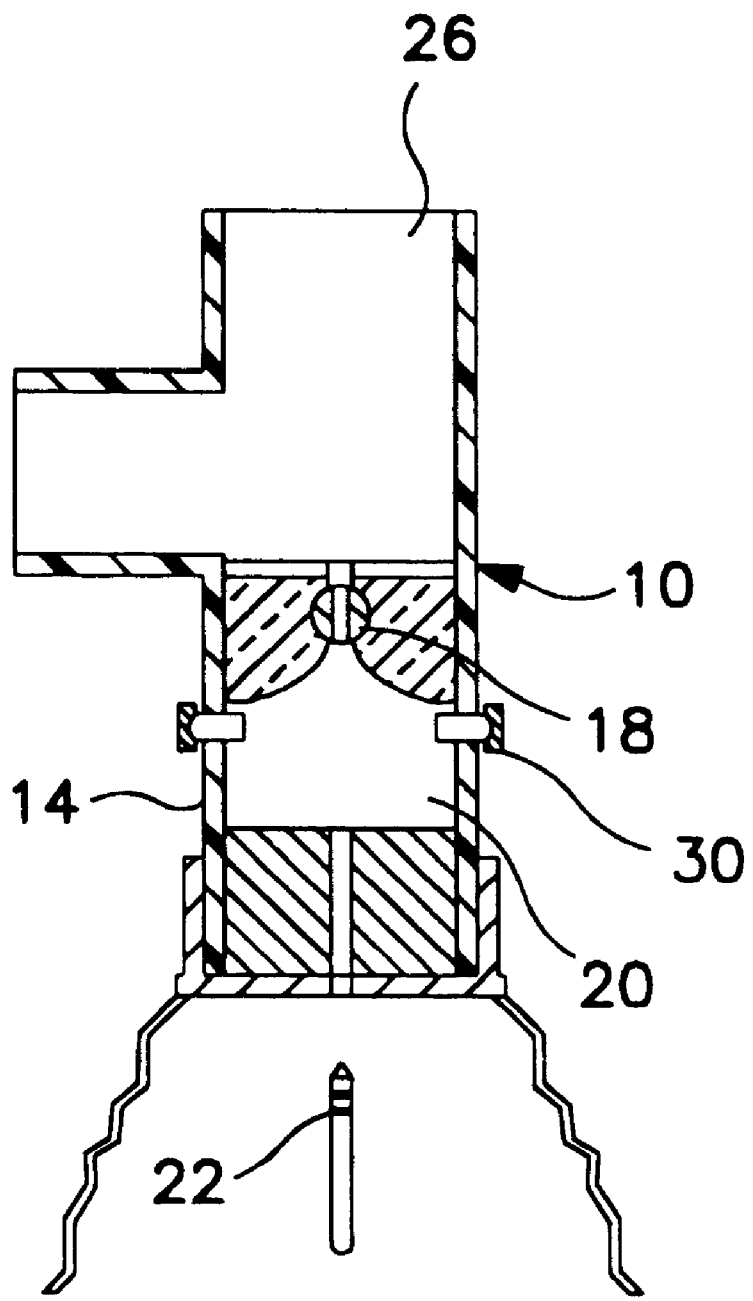
FIG. 1 shows a cross-sectional view of a manifold and catheter cleansing mechanism in accordance with the teachings of the prior art.

Referring to FIG. 1, there is shown a cross-sectional view of a manifold 10 and catheter cleansing mechanism 14 in accordance with the teachings of the prior art. The manifold has a valve mechanism in the form of a rotatable rod 18 for selectively isolating a lavage chamber 20 from the ventilation circuit 26. When the distal end of the catheter 22 is disposed in the lavage chamber 20, a lavage solution can be injected through a side port 30 to help wash the mucus and other secretions from the exterior of the catheter 22. References herein to "lavage solution" or "saline solution" should be construed to include similar irrigating or cleaning liquids recognized by those skilled in the art.

Because of the relative size and dimensions of the lavage chamber 20, however, there is nothing to force vigorous interaction between the saline solution and the secretions on the exterior of the catheter. Additionally, because the lavage chamber is not configured for makeup air to enter when the rotatable rod 18 is closed, a vacuum can be created in the lavage chamber 20 that interferes with effective suctioning. An additional disadvantage of the embodiment shown in FIG. 1 is that the closure mechanism for such devices typically must be manually activated. If the user fails to close the rotatable rod 18, actuation of suction through the catheter will draw air from the ventilation circuit 26.

Figure 2:
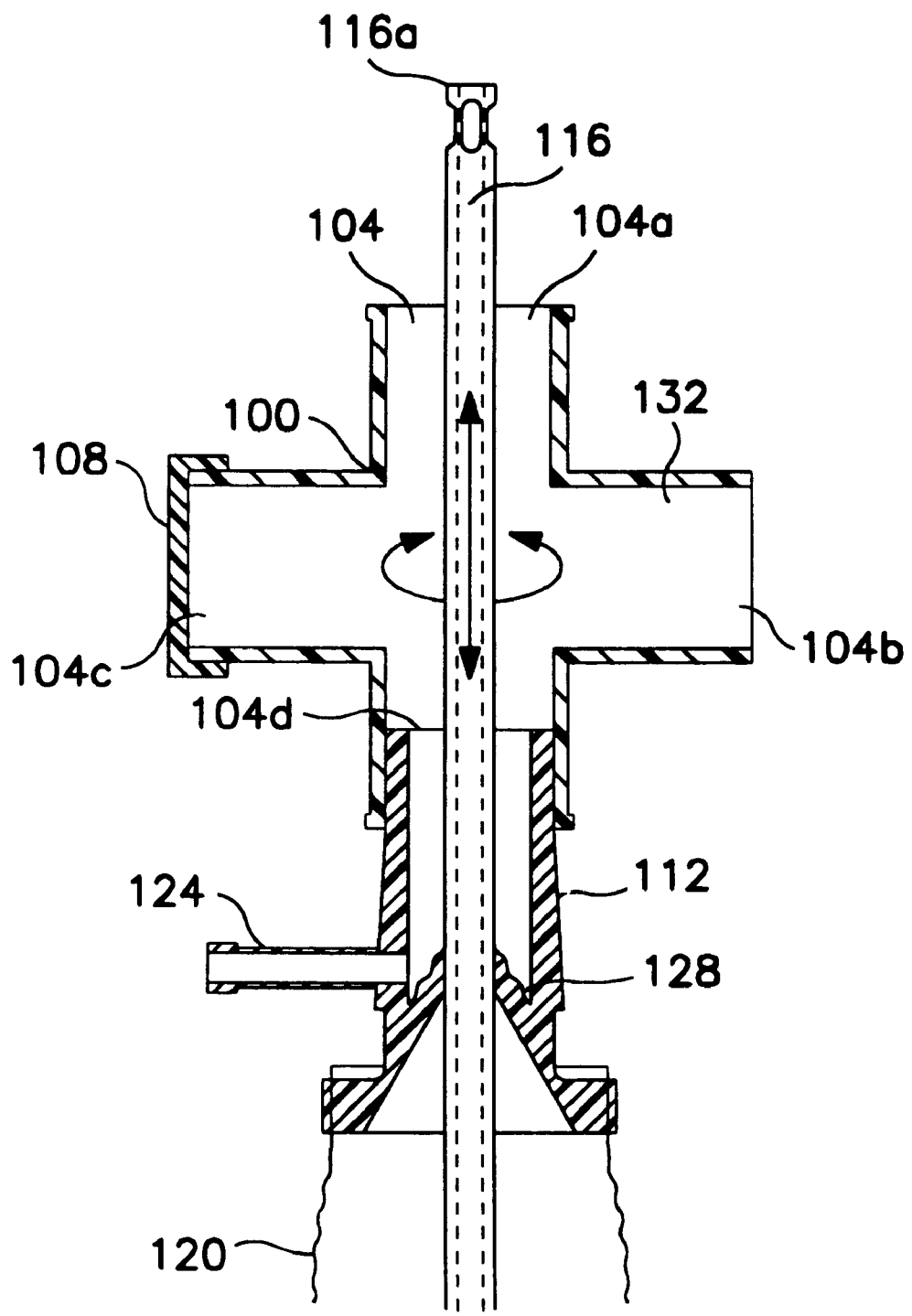
FIG. 2 shows a cross-sectional view of a manifold and catheter cleaning mechanism in accordance with the teachings of another embodiment of the prior art.

Turning now to FIG. 2, there is shown a cross-sectional view of an alternative embodiment of the prior art. The manifold 100 is provided with a plurality of ports 104. A first port 104a is attached to the hub of an endotracheal tube of the patient to conduct respiratory air to and from the endotracheal tube. Thus the manifold forms part of a ventilation circuit. The air is typically provided to and removed from the manifold through a second port 104b which is attached to a pair of ventilation tubes via a connector (not shown). The ventilation tubes are, in turn, connected to a mechanical ventilator (not shown) in a manner that will be well known to those skilled in the art.

A third port 104c may be situated opposite the second port 104b. The third port 104c is typically covered with a cap 108 which is removed when "blow-by" is desired to wean a patient from forced ventilation as subsequently discussed in more detail. The manifold may comprise a fourth port 104d.

A coupling 112 is configured to form a force-fit engagement with the fourth port 104d and effectively connects the catheter 116 and an optional protective sleeve 120 to the manifold 100. Disposed adjacent a proximal end of the coupling 112 is a lavage port 124 through which a cleaning liquid can be injected to rinse the exterior of the catheter 116. Such a configuration is advantageous because the lavage port 124 is positioned distal a seal 128. A user will typically withdraw the catheter 116 until the distal end 116a thereof is positioned slightly distally of the seal 128, and then the cleaning solution will be injected into the lavage port 124 to assist in the removal of secretions. While such a method of removing the secretions is generally effective, it can draw more air from the ventilation circuit 132 than is necessary to effectively clean the distal end 116a of the catheter 116. Additionally, it is common for respiratory therapists and other clinicians to maintain suction through catheter 116 during the withdrawal of catheter 116 from the first port 104a to a position immediately adjacent the seal 128.

Figure 3A:
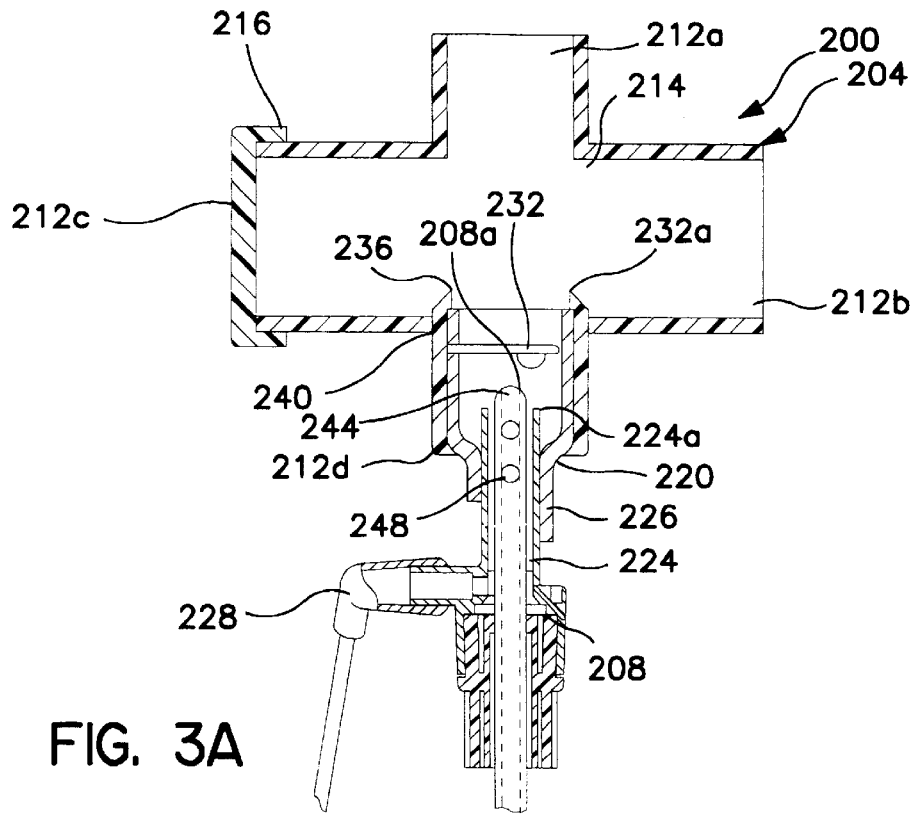
FIG. 3A shows a cross-sectional view of the manifold and distal portion of a catheter of an improved respiratory suction catheter apparatus with a valve member in an open position in accordance with the principles of the present invention.

Turning now to FIG. 3A, there is shown a cross-sectional view of a portion of an improved endotracheal catheter, generally indicated at 200. The endotracheal catheter includes a manifold, generally indicated at 204 and a catheter 208. The manifold 204 includes a plurality of ports 212a–d. A first port 212a is configured for attachment to the proximal end of an artificial airway, such as the hub of an endotracheal tube. A second port 212b is typically connected to a pair of ventilator tubes (not shown) by means of an adapter (not shown), in accordance with common practice in the art.

As used herein, distal refers generally to the direction of the patient, while proximal refers to the direction of the user. Unless otherwise noted, each figure is oriented such that the distal (patient) end is toward the top of the page, while the proximal (clinician) end is toward the bottom of the page.

During normal usage, conditioned inspiratory air is forced through one of the ventilator tubes, through the second port 212b and the first port 212a and into the patient's lungs via the artificial airway. Exhaled air is carried through the first port 212a and then the second port 212b and out through the other ventilator tube. Thus, the manifold 204 forms part of a ventilation circuit 214 through which respiratory air is cycled.

Also forming part of the manifold 204 is a third port 212c in this embodiment. A cap 216 typically covers the third port 212c. Whenever mechanical ventilation is used, it is the goal to eventually return the patient to voluntary or spontaneous breathing. To accomplish this, the patient must usually be weaned from the mechanical ventilation—to spontaneous breathing.

To this end, the cap 216 may be removed from the third port 212c so that oxygenated air is passed by the patient's endotracheal tube, but inspiratory air is not forced into the patient's lungs by means of a completely closed circuit. This situation, commonly called "blow-by," enables the patient to gradually resume natural or spontaneous breathing.

The manifold 204 may comprise a fourth port 212d as shown herein. The fourth port 212d is disposed generally opposite the first port 212a and is configured to allow the catheter 208 to slide therethrough and into the first port to enable suctioning of the patient. At the completion of suctioning, the catheter 208 is pulled back into the fourth port 212d to prevent interference with the ventilation circuit 214.

Disposed between the wall forming the fourth port 212d and the catheter 208 is a coupling or adapter 220. On an outer extreme, the adapter 220 engages the wall defining the fourth port 212d. On an inner extreme, the adapter 220 engages a collar 224 that closely surrounds the catheter 208 so as to leave a small cylindrical space 226 around the catheter 208. Ideally the space between the catheter 208 and the collar 224 is between about 0.127 mm (0.005 inches) and about 0.381 mm (0.015 inches).

This proximity provides two important advantages. First, if saline solution needs to be provided to the lungs of the patient, injecting saline solution through the lavage port 228 and into the cylindrical space 226 causes a stream of saline solution to be directed out the distal end 224a of the collar 224 and through the first port 212a typically after the catheter 208 has been at least partially advanced through manifold 204. If the spacing between the catheter 208 and the collar 224 is too large (as in the art discussed above), the saline solution cannot be directed. Second, as the catheter 208 is drawn back into the collar 224 after use, the collar helps to wipe any heavy layers of mucus or other secretions from the outside of the catheter.

Injecting saline solution through the lavage port 228 further removes the secretions from the exterior of the catheter 208 and enhances evacuation by suction in the catheter. This configuration also minimizes the volumes of air and cleaning solution necessary to effect cleaning.

While the collar 224 configuration shown in FIG. 3A is beneficial, it is still common to have secretions build up on the distal end 208a of the catheter 208. If such build up is not promptly removed, it can interfere with the ability of the catheter to properly suction the patient. It can also serve as a culture medium for pathogens within the closed suction catheter system. The present invention enhances the duration that the closed suction catheter system may be used by reducing the amount of pathogens on catheter 208 as disclosed herein.

In accordance with one of the principles of the present invention, it has been found that selective obstruction of the airflow into the distal end 208a of the catheter 208 significantly improves catheter cleaning. Additionally, it has been found that such a mechanism for improved cleaning process also minimizes the withdrawal of air from the ventilation circuit 214.

As shown in FIG. 3A, a flap 232 is hingedly attached to an annular ring 236 disposed inside the fourth port 212d so as to enable the flap 232 to pivot with respect to the ring to form a self-closing valve member. Of course, the flap 232 could be attached directly to the wall of the manifold 204 defining the fourth port 212d or to the adapter 220. The hinged attachment 240 allows the flap 232 to selectively move while maintaining alignment with the catheter tip, thereby creating a self-closing flap valve.

Figure 3B:
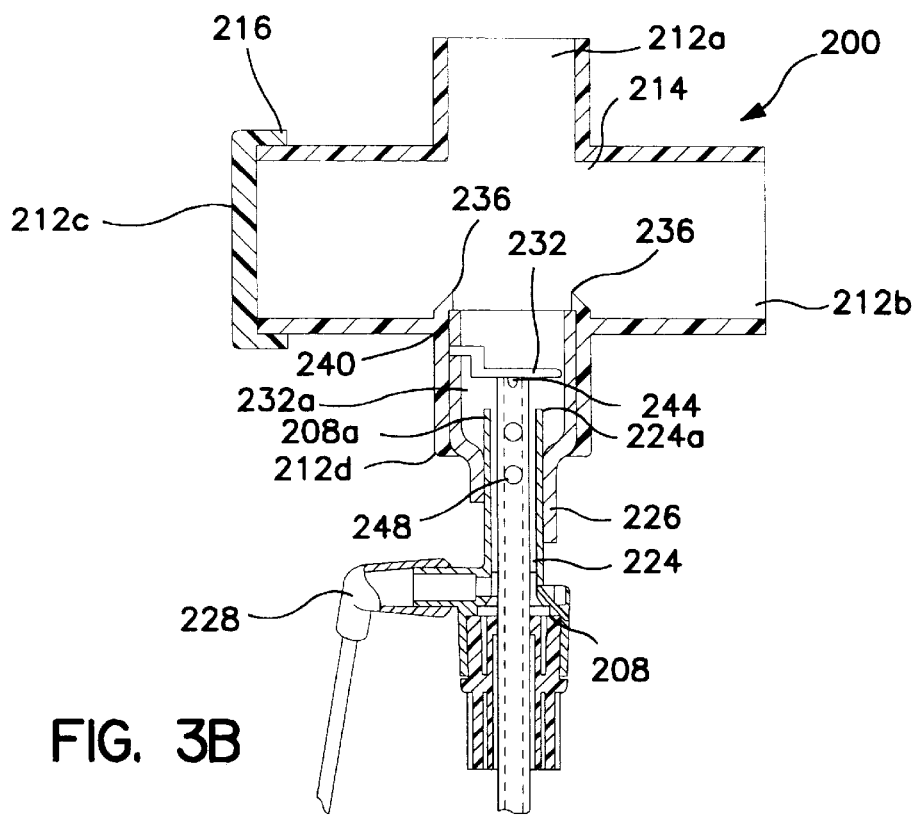
FIG. 3B shows a cross-sectional view of the manifold and catheter portion shown in FIG. 3A, with the valve in a second, closed position.

As shown in FIG. 3B, the flap 232 is positioned to align with the distal end 208a of the catheter 208 when the catheter is almost completely withdrawn into the collar 224.

The hinged attachment 240 is sufficiently flexible that suction through the distal end 208a of the catheter 208 will draw the flap 232 proximally from a first, distal position into a second, proximal position, wherein the flap contacts the distal end 208a of the catheter 208. Thus, the flap 232 and related structures form a self-closing valve wherein no additional external manipulation of the catheter system is needed to close the valve.

As with most closed suction catheters, the catheter 208 is formed such that a primary aperture 244 is formed in the distal end 208a and one or more lateral apertures 248 positioned slightly proximal from the distal end 208a. When the flap 232 moves proximally and contacts the distal end 208a of the catheter 208, suction through catheter tip aperture 244 is reduced or eliminated. The covering of aperture 244 causes increased suction flow in the lateral apertures 248, thereby increasing the evacuation of secretions contained between the outside of the catheter 208 and the interior of the collar 224 via apertures 248. Because each lateral aperture 248 is generally smaller than the distal aperture 244 and because the collar 224 limits airflow to the lateral apertures 248, less air is drawn from the ventilation circuit while simultaneously improving cleaning of the catheter 208.

As shown in FIGS. 3A and 3B, the proximal side 232a (i.e., the side opposite the ventilation circuit 214) of the flap 232 is generally planar. In such a configuration, the proximal side 232a of the flap 232 may form a substantially complete seal with the distal end 208a of the catheter 208 to selectively occlude the catheter 208 from the manifold 200.

Figure 3C:
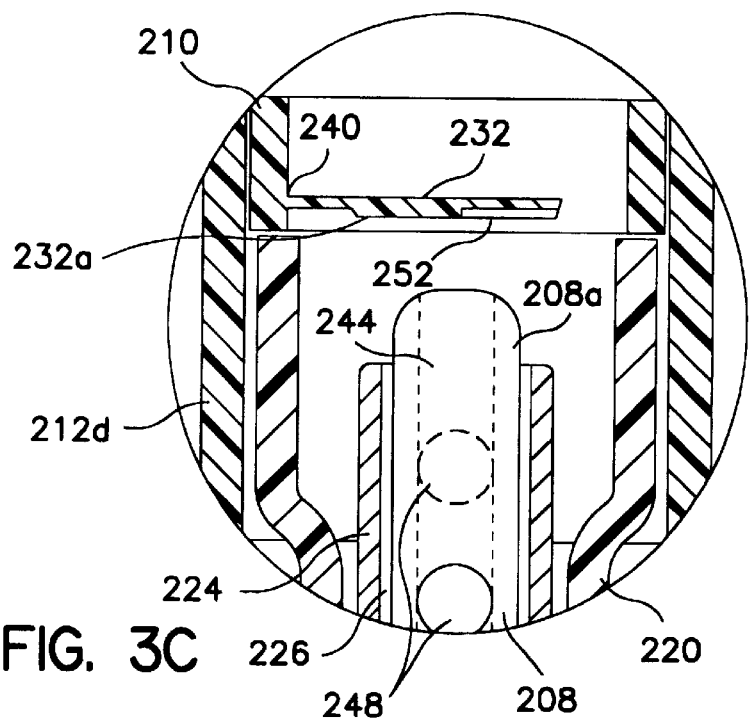
FIG. 3C shows a fragmented, close-up cross-sectional view of one embodiment of the improved respiratory suction catheter apparatus shown in FIG. 3A.

Turning now to FIG. 3C, there is shown a close-up cross-sectional view of the embodiment shown in FIGS. 3A and 3B with a slight modification to the flap 232. Unlike the flap 232 in FIGS. 3A and 3B which is substantially planar, the flap 232 in FIG. 3C has a channel 252 formed therein on the proximal side 232a. The channel 252 prevents the flap 232 from forming an airtight engagement with the distal end 208a of the catheter 208. In other words, the channel 252 ensures that a measured volume of air will be drawn into the aperture 244 at the distal most end 208 of the catheter.

The measured volume of air that is drawn in through the channel 252 can have an important effect. Specifically, the air creates turbulent airflow both within the catheter 208 and immediately around its exterior. The turbulent airflow in turn, assists in breaking up agglomerations of mucus and secretions which saline solution alone may not. Thus, the turbulent airflow helps to provide improved cleaning of the distal end 208a of the catheter 208. This is in sharp contrast to many of the prior art devices that have advocated the use of a lavage/cleaning chamber to clean the exterior of the catheter. Because the lavage/cleaning chamber is usually substantially larger than the catheter or because makeup air is not specifically provided, it is difficult to create turbulent airflow within the chamber. Without turbulent airflow, the mucus and other secretions are more difficult to remove from the exterior of the catheter.

Figure 3D:
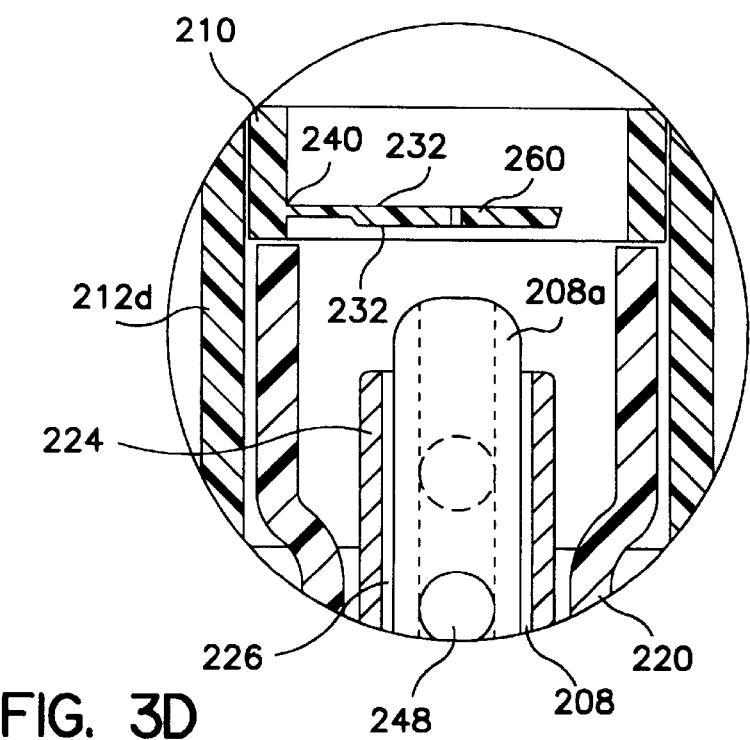
FIG. 3D shows a fragmented, close-up cross-sectional view of another embodiment of the improved respiratory suction catheter apparatus shown in FIG. 3A.

Turning now to FIG. 3D, there is shown yet another variation of the flap 232 shown in FIGS. 3A and 3B. Rather than having a channel formed in a proximal side 232a thereof, the flap 232 has an aperture 260 formed therein so as to allow a relatively small amount of air to pass through the flap 232. The small hole creates turbulent airflow at the distal end 208a of the catheter 208 and thereby improves cleaning. It is currently believed that an aperture 260 in the flap 232 with a diameter of about 0.76 mm (0.03 inches) is preferred.

Figures 3E, 4A:
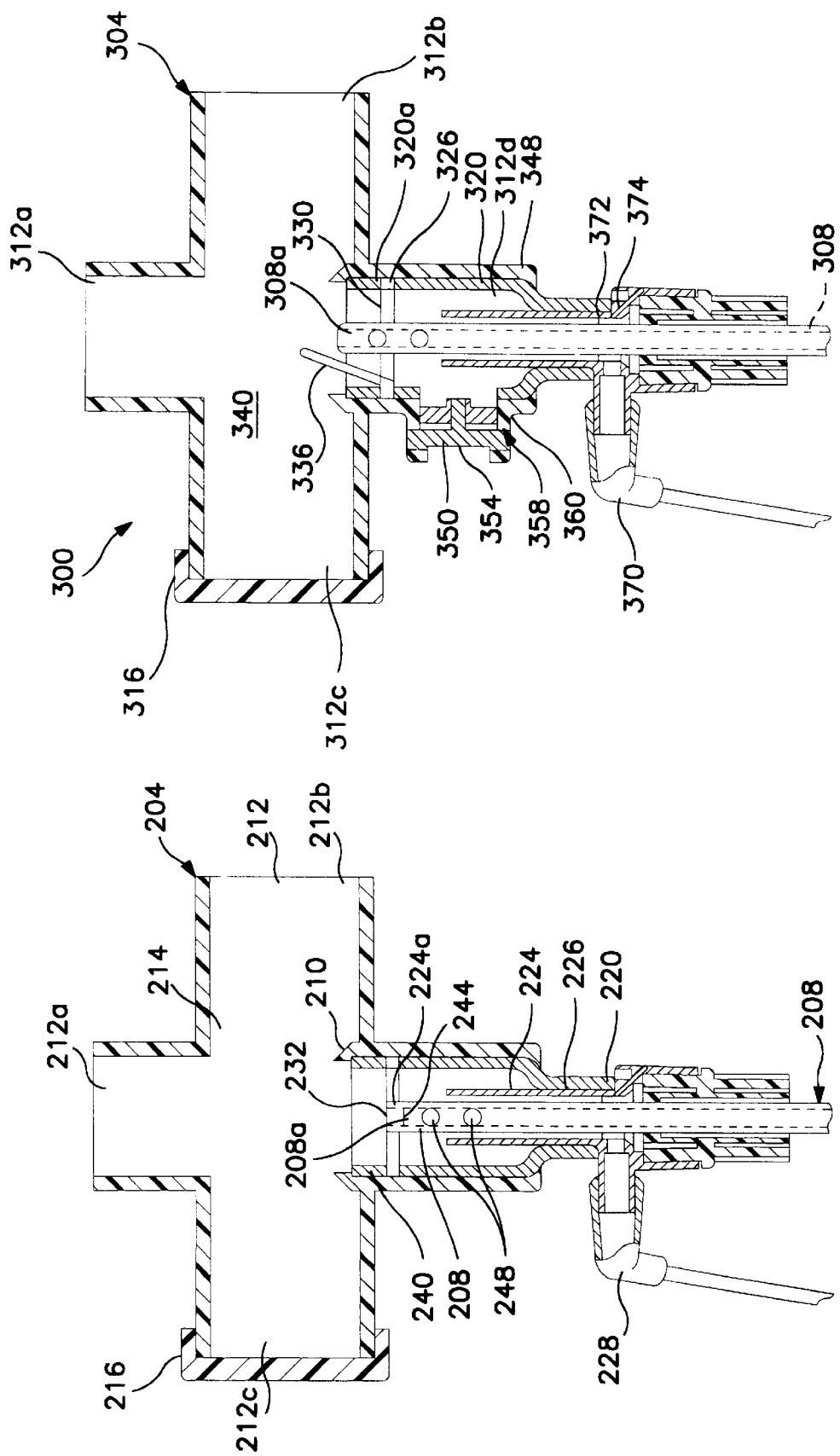
FIG. 3E shows a cross-sectional view similar to those shown in FIGS. 3A through 3D of an alternate embodiment wherein the seal engages the collar.
FIG. 4A shows a fragmented, cross-sectional view of an alternative embodiment of an improved respiratory suction catheter apparatus having a valve in an open position in accordance with the principles of the present invention.

While shown in FIGS. 3A through 3D as engaging the distal end 208a of the catheter 208, the flap 232 forming a flap valve need not engage the catheter itself. Thus, for example, FIG. 3E shows an embodiment similar to those shown in FIGS. 3A through 3D, except that the flap 232 is disposed to engage the distal end 224a of the collar 224 rather than the distal end 208a of the catheter 208. In such a configuration, suction flow can still be achieved through the aperture 244 at the distal end 208a of the catheter 208.

Preferably, a source of makeup air will be provided as will be discussed in greater detail herein in reference to FIGS. 4A, 4B, and 4C. This can be accomplished by using either of the flap configurations shown in FIGS. 3C and 3D. In the alternative, a small hole can be formed in the collar 224 to facilitate a small amount of makeup air being present to enhance suction flow and to increase turbulence.

Regardless of which configuration of those shown in FIGS. 3A through 3E is used, the result is an improved ability to clean the distal end 208a of the catheter 208, while at the same time significantly reducing the amount of air which is withdrawn from the ventilation circuit 214. Thus, consistent ventilation is provided to the patient and the clinician is able to more easily clean the catheter 208.

Turning now to FIG. 4A, there is shown another embodiment of an improved respiratory suction catheter apparatus, generally indicated at 300, made in accordance with the principles of the present invention. The improved respiratory suction catheter apparatus 300 includes a manifold 304 and a catheter 308. As with the previous embodiment, the manifold 304 includes a first port 312a, a second port 312b, a third port 312c, and a fourth port 312d, This embodiment may further comprise a cap 316 over at least one port, shown on port 312c in this configuration. An adapter 320 may be disposed in the fourth port 312d. The adapter 320 may be adhesively attached to the manifold 304, or may be a simple force-fit.

Unlike the embodiment discussed with FIGS. 3A through 3D, an annular ring is not disposed in the manifold 304 independent of the adapter 320. Rather, an annular ring 326 extends inwardly from a distal end 320a of the adapter 320. The annular ring 326 defines an aperture or opening 330 through which the catheter 308 can be extended. Thus, the opening 330 is slightly larger than the exterior of the catheter 308.

Also extending inwardly from the adapter 320 is a flap 336. The flap 336 is preferably hingedly attached to either the adapter directly or to the annular ring 326. When no suction is applied to the catheter 308, or when the distal end 308a of the catheter is disposed distally from the flap 336, the flap will generally extend distally from the annular ring 326 and provide virtually no resistance to advancement of the catheter 308. As discussed herein, flap 336 may benefit from the incorporation mechanism that biases flap 336 in a closed position when the catheter 308 is retracted. Moreover, flap 336 may be formed such that it is biased in this closed position.

Figure 4B:
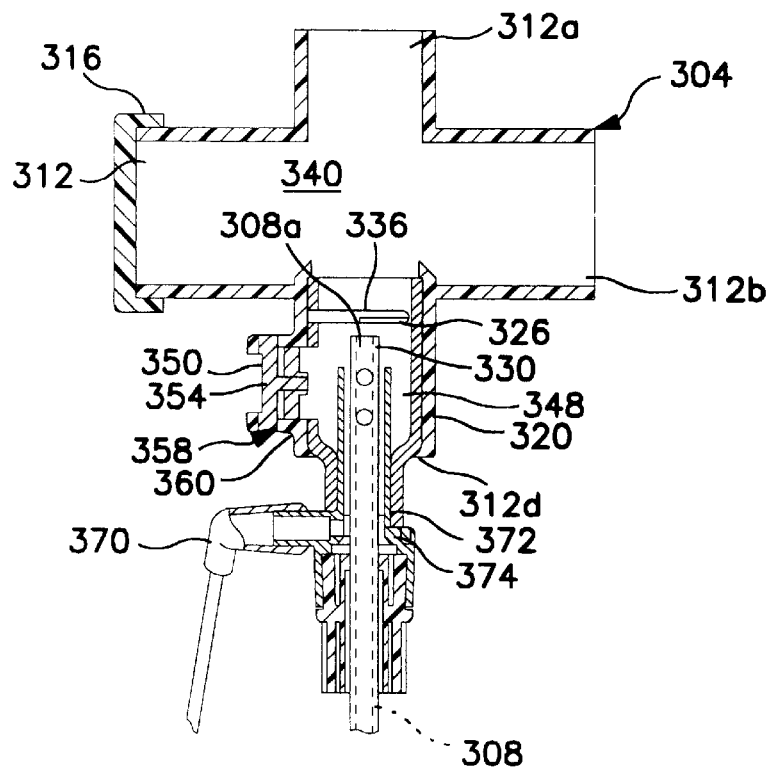
FIG. 4B shows a fragmented, cross-sectional view of the embodiment of FIG. 4A, wherein the valve is in a closed position to isolate the catheter from the ventilation circuit.

As shown in FIG. 4B, as the distal end 308a of the catheter 308 is withdrawn through the annular ring 326 while suction is applied, a vacuum is created which pulls the flap 336 over the opening 330, thereby isolating the distal end 308a of the catheter 308 from the ventilation circuit 340 and preventing the catheter from drawing air away from a patient to whom the manifold is attached. When the flap 336 is configured in the manner shown in FIGS. 3C and 3D, these configurations use makeup air from the ventilation circuit 340.

If the catheter 308 were simply left in chamber 348 behind the flap 336/annular ring 326 and saline solution were injected into the chamber, a substantial negative pressure could build within the chamber. Additionally, because no relief is provided, it would be difficult to suction mucus and similar substances from the chamber once the lavage source had been sucked dry. To overcome these problems with the prior art, the embodiment in FIGS. 4A through 4C has a makeup air inlet, generally indicated at 350 which is formed in a portion of the wall defining the fourth port 312d of the manifold and the adapter 320. The makeup air inlet 350 preferably includes a filter 354 that is selected to substantially prevent cross-contamination between the environment/clinicians and the patient. Disposed adjacent to the filter material is a flexible barrier 358 which forms a one-way valve 358.

Figure 4C:
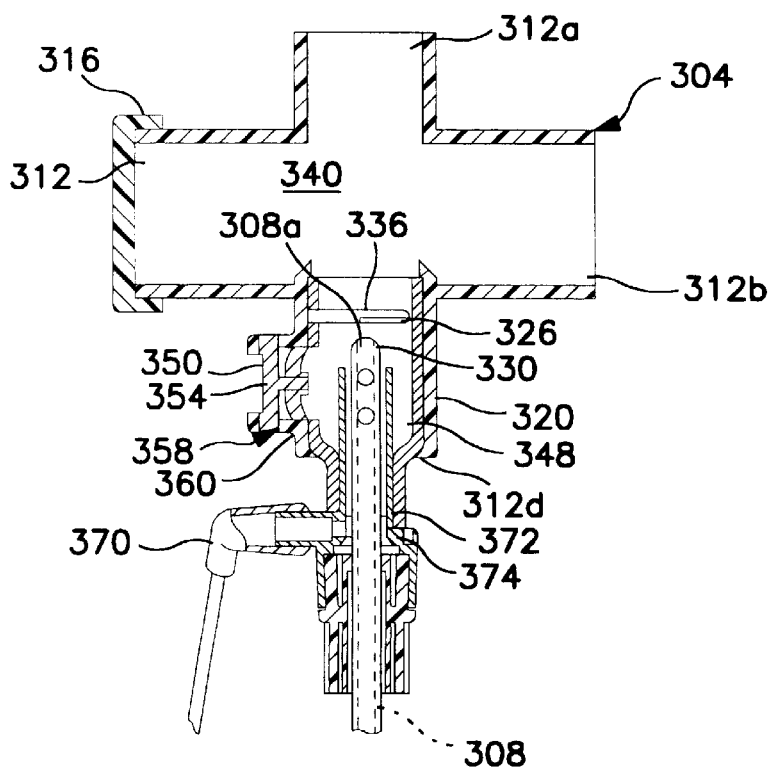

As shown in FIGS. 4B and 4C, the one-way valve 358 will generally be closed when the catheter 308 is in an extended position, wherein the catheter extends through the opening 330 in the annular ring 326. However, once the distal end 308a of the catheter 308 has been withdrawn through the opening 330 in the annular ring 326 and the flap 336 has been drawn closed, a vacuum will quickly develop on the side of the flap 336 opposite the ventilation circuit 340. The vacuum causes the one-way valve 358 to open and allow a supply of makeup air to enter the chamber. The makeup air flowing past the flexible one-way valve member 358, helps to create turbulent airflow and facilitate removal of any respiratory secretions on the catheter 308. This is preferably accomplished at about the same time the user utilizes the lavage port 370 to inject saline solution through the space 372 between the collar 374 and the catheter 308. It will be appreciated that the one-way valve 358 could be configured to provide very little resistance to air inflow, or could be configured to require a substantial vacuum to be present before makeup air is allowed into the area proximal the flap 336.

Turning now to FIG. 5A, there is shown a fragmented, cross-sectional view of an alternative embodiment of an improved respiratory suction catheter apparatus generally indicated at 400. The respiratory suction catheter apparatus includes a manifold 404 and a catheter 408 that is moveable through the manifold to suction secretions from a patient's lungs. As with the previously discussed embodiments, the manifold includes a first port 412a for attachment to an endotracheal tube or other artificial airway, a second port 412b for attachment to the ventilator tubes of a mechanical ventilator, an optional third port 412c that is covered with a cap 416, and an optional fourth port 412d which receives the connector or adapter 420.

Disposed at the distal end 420a of the adapter 420 is a valve 424 in a configuration that is commonly referred to as a duckbill valve. The valve 424 is formed by a piece of resilient material that opens as the catheter 408 is advanced therethrough, and closes when the catheter is withdrawn. The valve 424 is attached to the adapter 420 by a flexible base 428.

Also disposed in the adapter 420 is an air inlet 432 which includes a filter material 436 and a resilient member 440 configured to form a one-way valve 444 similar to that discussed in the previous embodiment. While duckbill valves have been used in endotracheal catheter systems in the past, the valve 424 shown in FIGS. 5A through 5C is substantially advanced in several respects. First, as shown in FIGS. 5A and 5C, the interior of the valve 424 has helical grooves 450 formed therein. The helical grooves 450 help to create turbulent airflow around the distal end 408a of the catheter 408. Additionally, the flexible base 428 is configured to allow the valve 424 be drawn toward the collar 460 to reduce the size of the cleaning chamber and improve removal of secretions from the exterior of the catheter 408.

Turning now specifically to FIG. 5B, there is shown a cross-sectional view similar to that shown in FIG. 5A, but with the distal end 408a of the catheter 408 in a retracted position. Once the distal end 408a of the catheter 408 is withdrawn proximally from the valve 424, the suction through the catheter works against the flexible base 428 of the valve and draws the valve toward the collar 460. A pair of air inlets 470 is disposed at the base 428 of the valve 424 and allows air into the valve.

Applying suction to the valve 424 and through the air inlets 470 as shown in FIG. 5B creates a vacuum between the adapter 420 and the flexible base 428, thereby causing the one-way valve 444 to open and allow air into the air inlets 470 at the top of the collar 460. This air mixes with the saline solution injected through the lavage port 490 and turbulently travels along the distal end 408a of the catheter 408. The turbulent motion of the air/saline mixture is enhanced by the helical grooves 450.

Once suction through the catheter 408 is stopped, there is no longer a negative pressure from the catheter to keep the one-way flap valve 444 opened, or to maintain the valve 424 adjacent to the distal end of the collar. Thus, the valve 424 may return to the position shown in FIG. 5A, except that it will be closed as the catheter 408 remains substantially in the collar until the next use.

Figure 6A:
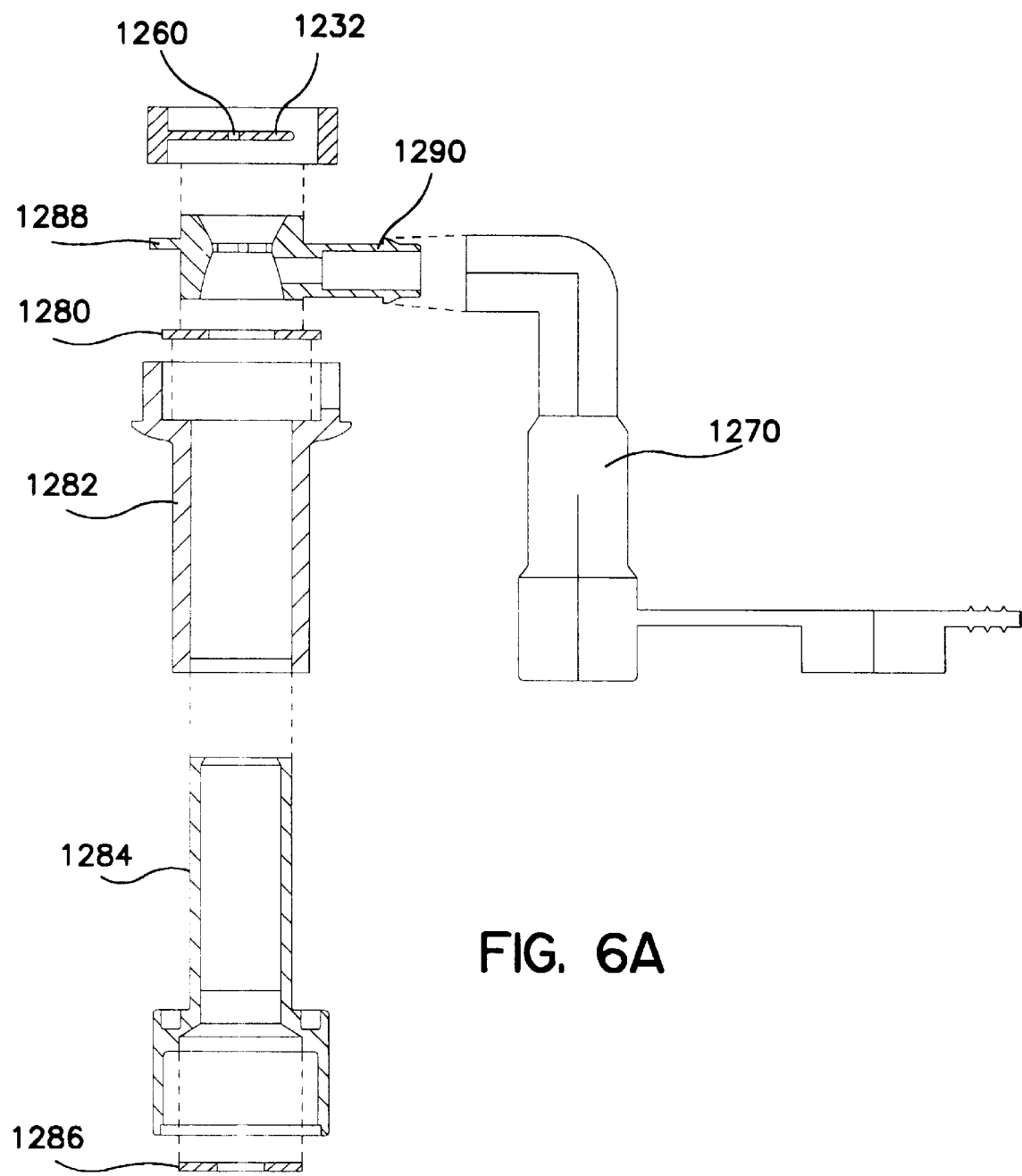
FIG. 6A shows an exploded, partial, cross-sectional view of a preferred embodiment of an improved respiratory suction catheter apparatus comprising a seal for wiping contaminants from the distal end of the catheter.

Turning to FIG. 6A, there is shown a partial, cross-sectional, exploded, cross-sectional view of a preferred embodiment of an improved endotracheal catheter made in accordance with the principals of the invention. As shown, this exploded assembly comprises a positive end expiratory pressure ("PEEP") or pressure seal 1286 or similar resiliently closing membrane that is disposed within manifold adapter 1284. As shown, the pressure seal 1286 rests within a cavity defined by manifold adapter 1284. As such, manifold adapter 1284 in turn may be inserted within a cavity formed within seal retainer 1282. Seal retainer 1282 is also formed to encompass wiper seal 1280 or similar resiliently closing membrane when assembled. This wiper seal 1280 will be discussed in greater detail below.

In turn, valve retainer 1288 presses wiper seal 1280 within the cavity formed in seal retainer 1282. In this configuration, valve retainer 1288 preferably comprises a lavage port 1290. Lavage port 1290 allows the connection of irrigation housing 1270. Moreover, valve retainer 1288 also prevents valve 1232 from being disposed more proximally than the closed position previously defined. Of note, valve 1232 further comprises an optional hole 1260 to improve cleaning as discussed herein.

Figure 6B:
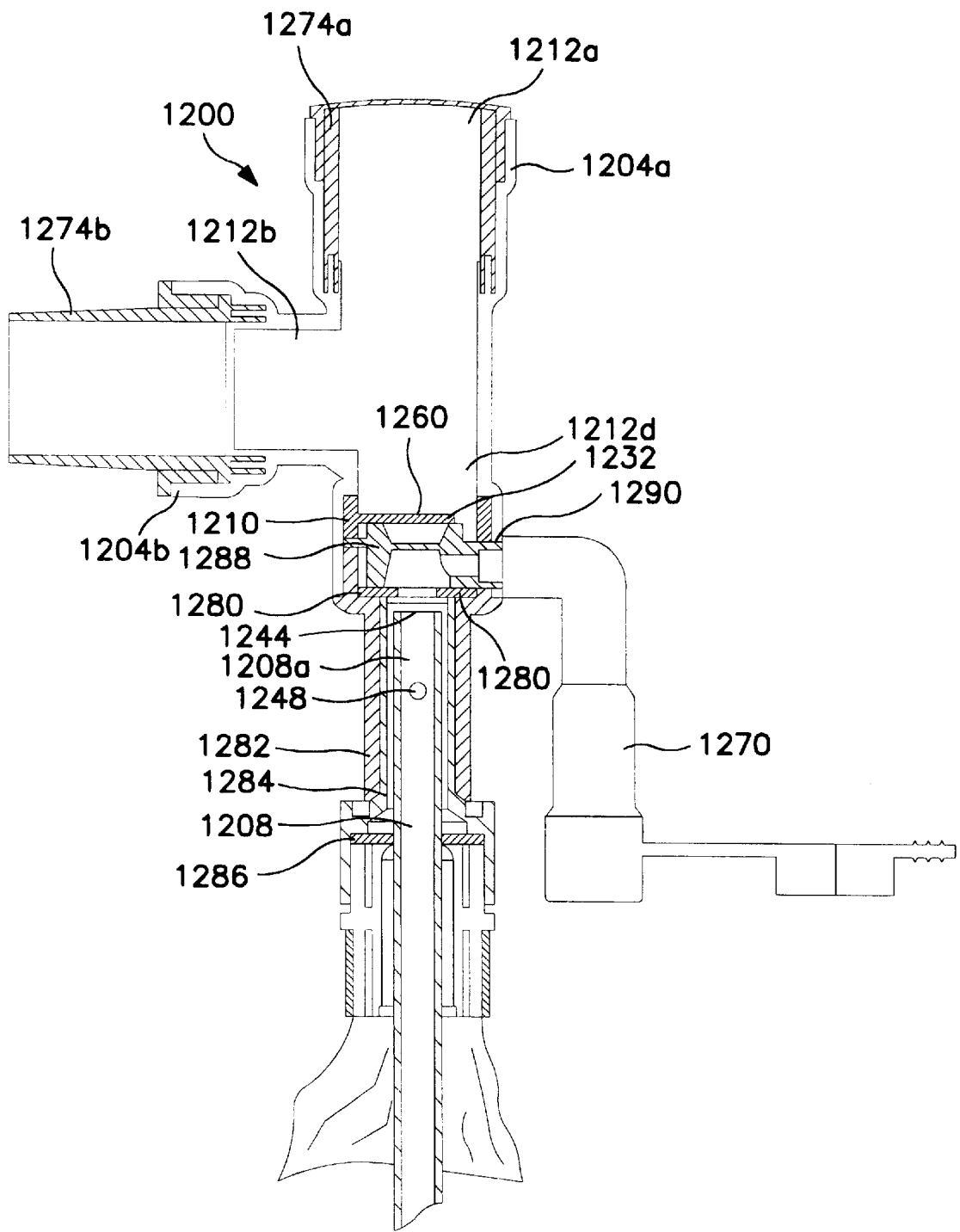
FIG. 6B shows a partial, cross-sectional view of an improved respiratory suction catheter apparatus having a seal for wiping contaminants from the distal end of the catheter.

Turning to FIG. 6B, a partial, cross-sectional view of a preferred embodiment of the invention, there is shown a preferred embodiment of the present invention as assembled. As shown, housing 1200 comprises three ports, port 1212a, 1212b, and 1212d. Those skilled in the art will recognize that a more or less ports, such as the inclusion of a fourth port, 1212c not shown, may be incorporated to allow greater flexibility and use. Moreover, as shown, ports 1212a and 1212b may be formed such that they may accommodate swivel connections. As shown, ports 1212a and 1212b are formed at swivel connection points 1204a and 1204b, respectively, to accommodate swivels 1274a and 1274b, respectively. In this configuration, the patient is allowed a greater freedom of movement and less discomfort related to binding, ill-fitting connections. Moreover, manipulation of the assembly by clinicians is more comfortable for the patient.

Moreover, as previously shown in FIG. 6A, FIG. 6B shows the pressure seal 1286 firmly seated within manifold adapter 1284. As shown after a portion of the exterior surface of the catheter 1208 is in contact with pressure seal 1286. Moreover, manifold adapter 1284 is shown disposed within seal retainer 1282. Though these portions may be fused together, it is advantageous to releasably connect these portions to allow for greater flexibility and accommodation of different configurations of an improved respiratory suction catheter apparatus.

As shown in FIG. 6B, the distal end 1208a of catheter 1208 is approaching wiper seal 1280. An aperture 1244 formed in the distal end 1208a of catheter 1208 provides a point of suction. Moreover, each additional aperture 1248, if included, may provide an additional point of suction. As shown in this assembled configuration, valve retainer 1288 presses wiper seal 1280 in a position such that the advancement of catheter 1208 will not dislodge wiper seal 1280. Furthermore, the valve retainer 1288 prohibits valve 1232, preferably the flap valve described herein, from moving to a position more proximal than the closed position. In this configuration, flap valve 1232 is connected to collar 1210 but any other configurations disclosed herein are considered within the scope of the invention as shown. Moreover, flap valve 1232 further comprises an optional hole 1260 formed therein to improve cleaning as previously discussed. Additionally, lavage port 1290 provides an attachment site for irrigation housing 1270. Irrigation housing 1270 may be force fitted or otherwise attached to lavage port 1290 to provide for an additional conduit for irrigation during the cleaning process.

Figure 6C:
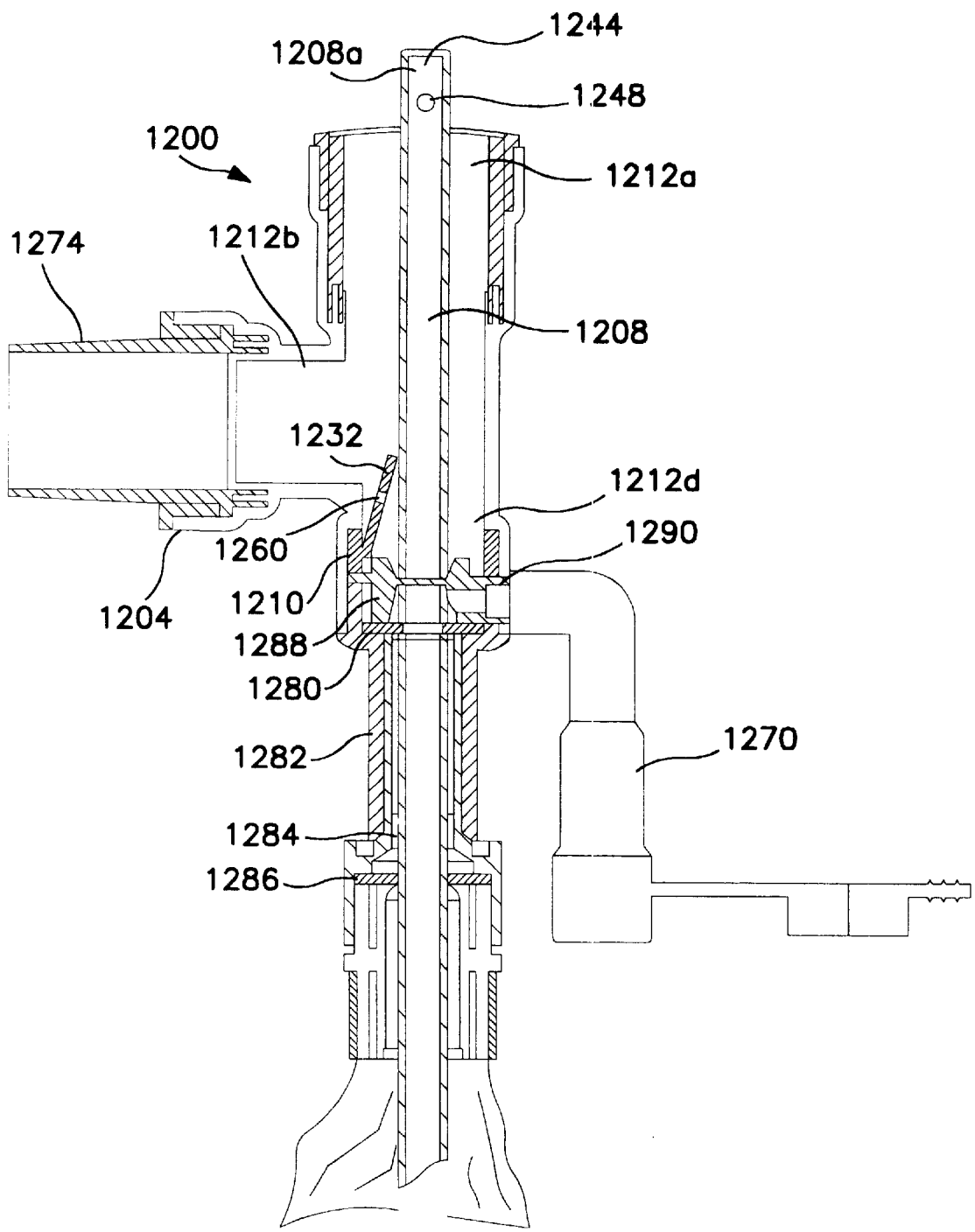
FIG. 6C shows a partial, cross-sectional view of a preferred embodiment of an improved respiratory suction catheter apparatus comprising a seal for wiping contaminants from the distal end of the catheter wherein the catheter is extended beyond the assembly.

With reference to FIG. 6C, a partial cross-sectional view of an improved respiratory suction catheter apparatus, catheter 1208 has translated through the manifold 1200 such that the distal end 1208a of catheter 1208 is available to enter the respiratory tract of a patient. It is envisioned that aperture 1244 and optional apertures 1248 may provide a point of suctioning. Of note, flap valve 1232 has been deflected to an open position to allow the translation of catheter 1208 therethrough. In this configuration, wiper seal 1280 contacts at least a portion of the exterior surface of catheter 1208 such that wiper seal 1280 may aide in the cleaning of catheter 1208 during retraction from patient. As shown, as catheter 1208 is retracted, wiper seal 1280 may engage and remain in contact with the portion of an exterior surface of the catheter 1208 during retraction. As catheter 1208 is retracted, wiper seal 1280 will effectively scrape mucus and other secretions from the exterior surface of catheter 1208.

Additionally, the benefits of wiper seal 1280 are further enhanced by alternative embodiments of valve 1232. As shown in FIG. 6D, a partial, exploded, cross-sectional view of the preferred embodiment of a respiratory suction catheter apparatus, valve 1232, including at least one protrusion 1292 extending beyond a planer surface of valve 1232, may increase the effectiveness of cleaning catheter 1208 as is shown in more detail herein with reference to FIG. 6G.

Figure 6E:
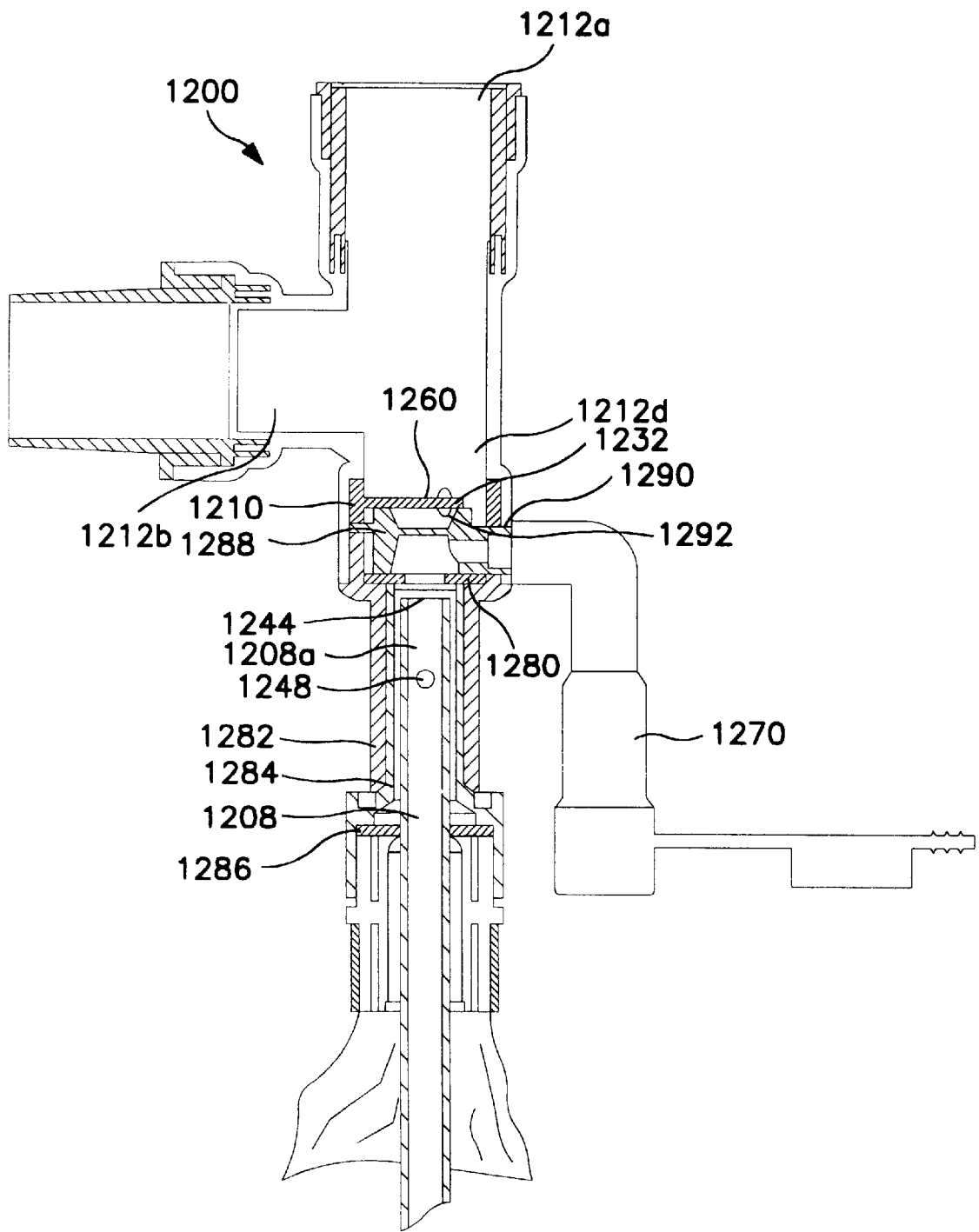
FIG. 6E shows a partial, cross-sectional view of an improved respiratory suction catheter apparatus comprising a seal for wiping contaminants from the distal end of the catheter and an alternative embodiment for a valve.

Specifically, as shown in FIG. 6E, a partial, cross-sectional view of a preferred embodiment of a suction catheter apparatus, the distal tip 1208a is advanced to wiper seal 1280 when catheter 1208 is advanced. As catheter 1208 passes through wiper seal 1280, a portion of the exterior surface of catheter 1208 coines into contact with wiper seal 1280 as shown in FIG. 6F, a partial cross-sectional view of the new preferred embodiment of the respiratory suction catheter apparatus.

Figure 6F:
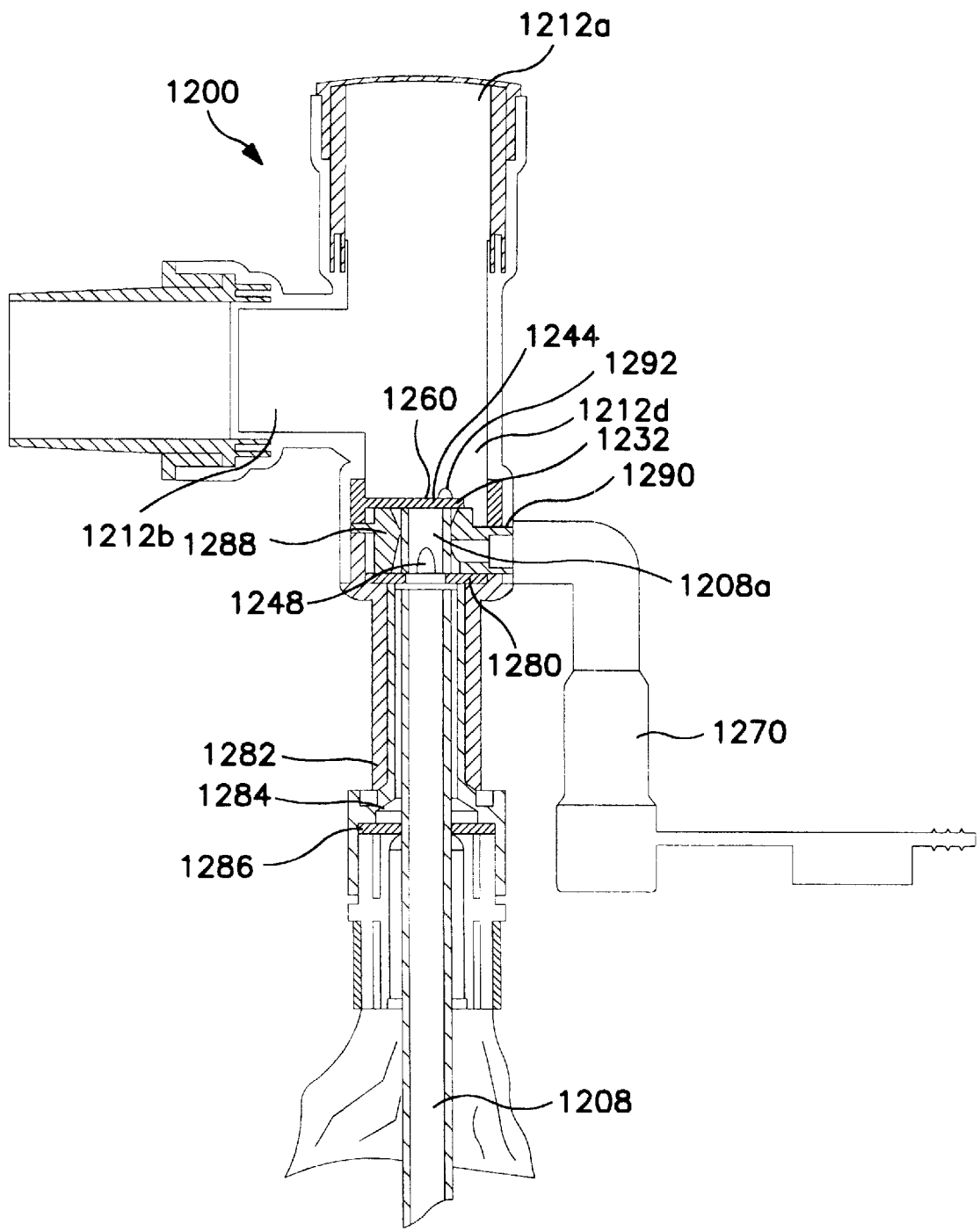
FIG. 6F shows a partial, cross-sectional view of an improved respiratory suction catheter apparatus comprising a seal for wiping contaminants from the distal end of the catheter and an alternative embodiment of the valve.

In FIG. 6F, catheter 1208 is advanced and comes into contact with a proximal surface of valve 1232. As previously discussed, this contact with valve 1232 will reduce the suction at aperture 1244 and allow greater suction via apertures 1248, if included, to improve cleaning of catheter 1208.

Though catheter 1208 is being advanced at this time, when catheter 1208 is retracted, the view as shown in FIG. 6F will occur again. Typically, the suction at the distal end 1208a of catheter 1208, occurring through aperture 1244, may assist flap valve 1232 to come into contact and form the closed position as shown in FIG. 6F. In this embodiment, an optional hole 1260 has been incorporated into flap valve 1232 to improve the cleaning effect after retraction.

As shown, the wiper seal 1280 will scrape mucus and similar secretions from the exterior surface from catheter 1208 during retraction. The availability of suction to remove this mucus and secretions improves the cleaning process. This arrangement reduces the opportunity for catheter 1208 to transfer mucus or similar secretions onto a distal surface of valve 1232. Moreover, the irrigation housing 1270 attached at lavage port 1290 of valve retainer 1288 provides an opportunity for cleaning solutions to be introduced to help dislodge mucus and similar secretions from the exterior surface of catheter 1208.

Figure 6G:
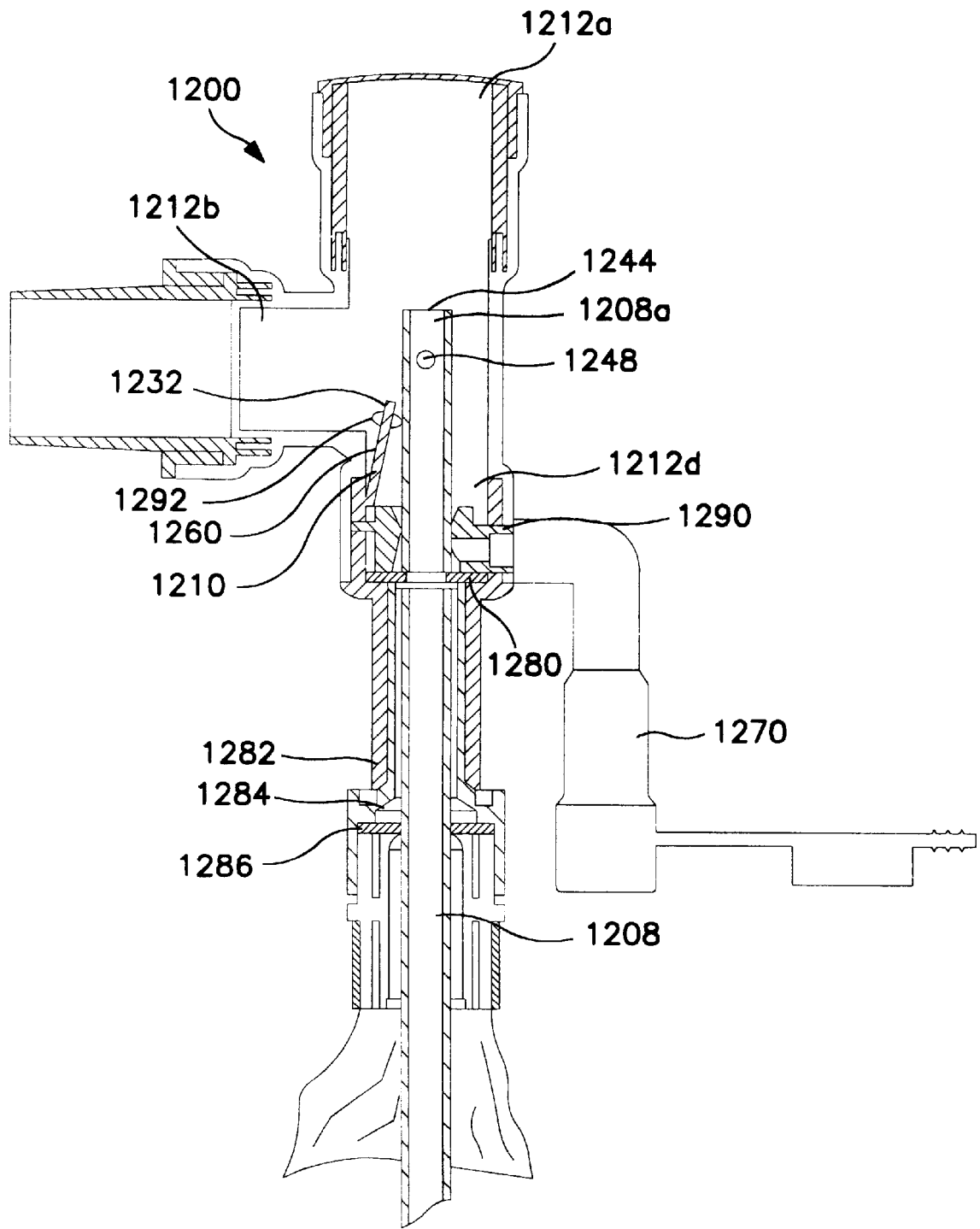
FIG. 6G shows a partial, cross-sectional view of a preferred embodiment of an improved respiratory suction catheter apparatus comprising a seal for wiping contaminants from the distal end of the catheter and an alternative embodiment of the valve displaced by the catheter advanced through the apparatus.

With reference to FIG. 6G, at least one protrusion 1292 on flap valve 1232, namely a protrusion 1292 formed on a proximal surface of flap 1232, when formed on flap 1232, aids in distancing the flap 1232 from catheter 1208 during advancement and retraction. Specifically, at least one protrusion 1292 formed on a proximal surface of flap 1232 may provide the primary point of contact between an exterior surface of catheter 1208 and the flap 1232 such that when catheter 1208 is retracted, protrusion 1292 comes into contact with catheter 1208. In this configuration, less mucus and similar secretions are scraped by the planar surface of flap 1232. This configuration reduces the likelihood that catheter 1208 will transfer mucus or similar secretions onto a distal surface of valve 1232. Therefore, more of the mucus and similar secretions are allowed to enter the cleaning chamber defined by valve 1232 in a closed position and pressure seal 1286 such that mucus and similar secretions may be cleaned during the cleaning process. Importantly, the inclusion of wiper seal 1280 will allow a significant portion of the mucus and similar secretions to be dislodged during retraction of catheter 1208 through manifold 1200.

Figure 6H:
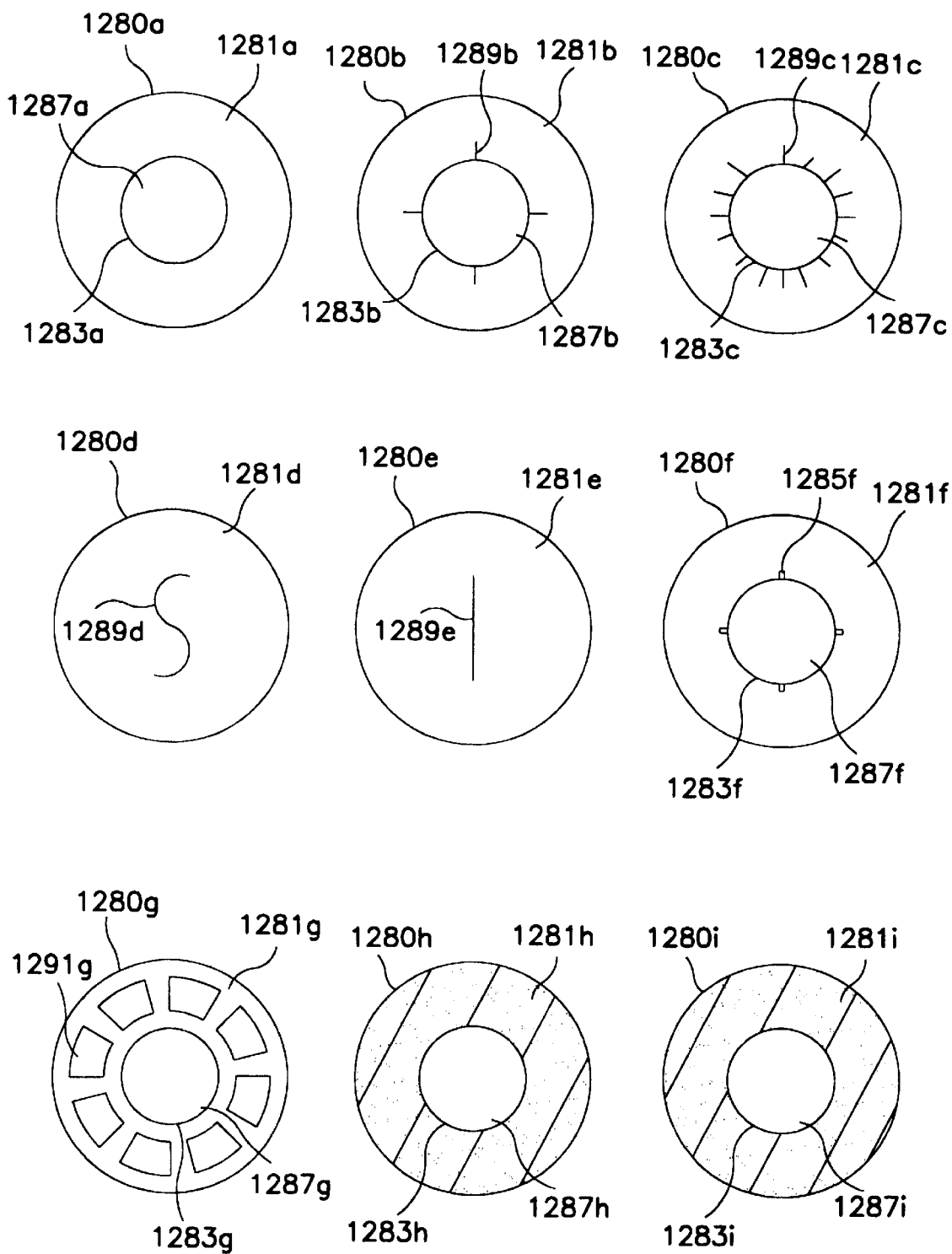
FIG. 6H shows cross-sectional, top views of several different configurations for the seal.

To this end, a variety of configurations in the formation of wiper seal 1280 are available. As shown in FIG. 6H, a cross-sectional, top view of several embodiments of wiper seal 1280, a variety of shapes and configurations may be used independently or in combination to form at least one wiper seal 1280.

Specifically, wiper seal 1280a as shown in FIG. 6H comprises a circular surface 1281a wherein a through hole 1287a, formed in a circular shape in this configuration, has been formed therein. It is preferable that the diameter in the through hole 1287a is slightly less than or equal to the outer diameter of catheter 1208 (not shown) such that the exterior surface of catheter 1208 (not shown) will contact a significant portion of the interior edge 1283a of surface 1281a of wiper seal 1280a.

As shown in wiper seal 280b, the wiper seal surface 1281b is formed such that a through hole 1287b is formed. Additionally, at least one slit 1289b is formed in surface 1281b to accommodate varying diameters of catheters that are advanced and retracted by through hole 1287b. As before, the advancement and retraction of catheter 1208 will come into contact with a significant portion of the edge 1283b of wiper seal surface 1281b.

Turning to wiper seal 1280c, wiper seal 1280c comprises a surface 1281c that forms a similar through hole 1287c. Moreover, this embodiment shows a significant plurality of slits 1289c formed within surface 1281c of wiper seal 1280c. In this configuration, the inner edge 1283c of surface 1281c of wiper seal 1280c remains extremely flexible and may accommodate the advancement and retraction of catheters of diameters of varying greater variance in size. As before, it is better for the diameter of through hole 1287c to be less than or equal to the exterior diameter of a catheter 1208 (not shown) that will be advanced and retracted therethrough.

Turning to wiper seal 1280d, the surface 1281d of wiper seal 1280d comprises an S-shaped slit 1289d formed therein. The advancement and retraction of the catheter 1208 (not shown) will expand and create a through hole through S-shape slit 1289d.

Similarly, wiper seal 1208e comprises a surface 1281e with a straight slit 1289e therein. Similarly, a catheter 1208 (not shown) will separate slit 1289e and allow for the retraction and advancement of catheter 1208 (not shown).

Alternatively, wiper seal 1280f comprises a surface 1281f formed such that a through hole 1287f is formed therein. The inner edge 1283f of surface 1281f will engage and contact catheter 1208 (not shown) as it passes therethrough. Of note, surface 1281f of wiper seal 1280f further comprises at least one notch 1285f formed about the inner edge 1283f of wiper seal 1280f. Each notch 1285f allows for the accommodating varying sizes of catheters 1208 (not shown) by allowing for a slightly greater diameter catheter 1208 to advance and retract therethrough.

In addition, wiper seal 1280g comprises a surface 1281g formed such that a through hole 1287g is formed therein. The inner edge 1283g of surface 1281g will engage in contact and catheter 1208 (not shown) as it passes therethrough. Of note, surface 1281g of wiper seal 1280g further comprises at least one cutout 1291g formed in surface 1281g. As shown, wiper seal 1280g comprises a plurality of cutouts 1291g to form a wagon-wheel appearance.

Turning to wiper seal 1280h, a configuration similar to wiper seal 1280a is shown. Specifically, wiper seal 1280h comprises a surface 1281h a through hole 1287h formed therein. This wiper seal 1280h is formed such that an inner edge 1283h of wiper seal 1280h may interact with a catheter 1208 (not shown) as it is advanced or retracted therethrough. Of note, wiper seal 1280h is shown in a cross-sectional view such that a sponge like or similar coarser material may be used in wiper seal 1280h.

Alternatively, wiper seal 1280i comprises a surface 1281i formed such that a through hole 1287i is formed therein and creates an inner edge 1283i in wiper seal 1280i to contact a catheter 1208 (not shown) during advancement nor retraction. This cross sectional view shows that brush like or similar materials may be used in the formation of wiper seal 1280i.

Figure 7:
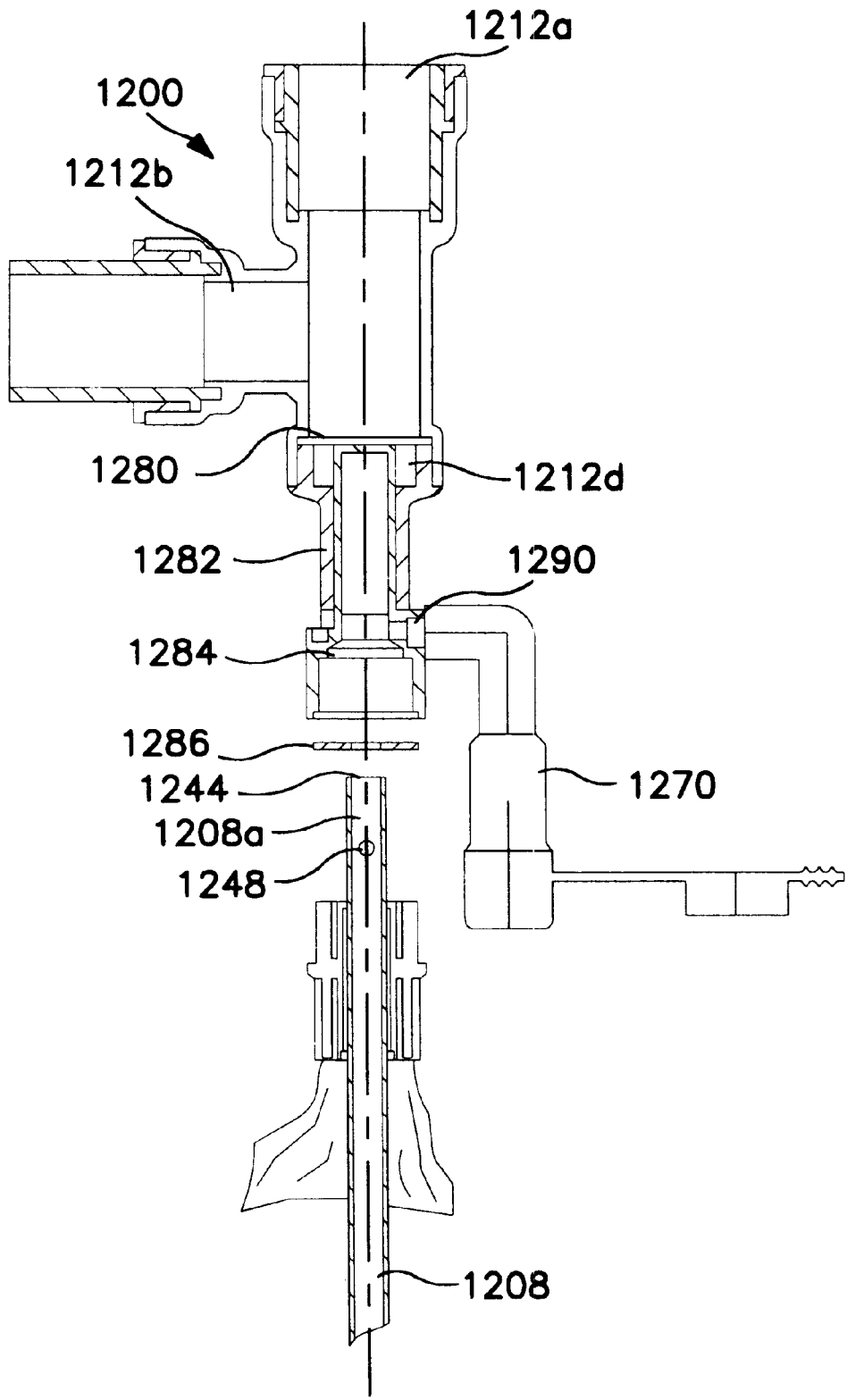
FIG. 7 an exploded, partial, cross-sectional view of an improved respiratory suction catheter apparatus comprising an alternative arrangement of seals to form the cleaning chamber.

With regard to FIG. 7, there is shown a partial, cross-sectional, exploded, cross-sectional view of a alternative embodiment of an improved endotracheal catheter made in accordance with the principals of the invention. As shown, this exploded assembly comprises a pressure seal 1286 or similar resiliently closing membrane that is disposed within manifold adapter 1284. The pressure seal 1286 rests within a cavity defined by manifold adapter 1284. As such, manifold adapter 1284 in turn may be inserted within a cavity formed within seal retainer 1282. Seal retainer 1282 is also formed to encompass wiper seal 1280 or similar resiliently closing membrane when assembled.

In this configuration, lavage port 1290 is disposed between wiper seal 1280 and pressure seal 1286 to form the cleaning chamber in this embodiment. Lavage port 1290 allows the connection of irrigation housing 1270. Of note, this configuration allows for an assembly without the need for a valve as shown in the other embodiments.

Turning now to FIGS. 8A and 8B, there is shown yet another endotracheal catheter embodying principles of the present invention. The respiratory suction catheter apparatus 600 includes a manifold 604 and a catheter 608 that is moveable through the manifold. As with many of the embodiments discussed previously, the manifold 604 includes a first port 612a for connection to the hub of an endotracheal tube, a second port 612b for connection (via ventilator tubes) to a mechanical ventilator, and an optional third port 612c and cap 616 which can be used for blow-by.

The fourth port 612d is different from those discussed previously because it has a shroud 620 placed therein. The shroud 620 is attached to a plunger 624 so as to allow the user to move the shroud between a first position adjacent the sidewall of the fourth port 612d (FIG. 8A) and a second position (FIG. 8B) wherein the shroud is disposed approximately at the center of port 612d.

During use of the respiratory suction catheter apparatus 600, the shroud 620 will typically be moved into the first position so that it does not interfere with advancement of the catheter 608 through the manifold 604. Once suctioning has been completed, the catheter 608 is withdrawn into the collar 634.

The plunger 624 is then pressed so as to move the shroud 620 over the distal end 634a of the collar 634 to cover the distal end 608a of the catheter 608. Typically, the catheter 608 will then be advanced toward the distal end 620a of the shroud 620. Lavage/cleaning solution will then be applied through the lavage port 640 while suction is applied.

If desired, a small gap can be formed between the shroud 620 and the collar 634 to ensure turbulent airflow into the distal end 608a of the catheter 608. Likewise, grooves or some other pattern may be formed in the shroud to encourage turbulent airflow. Additionally, a valve member may be included to allow for makeup air in a similar manner as discussed with several of the embodiments above.

Of note, both FIG. 8A and FIG. 8B show an apparatus 600 that benefits from the inclusion of wiper seal 680. In this configuration, wiper seal 680 acts to scrape mucus and similar secretions from catheter 608 during retraction.

Figure 9A:
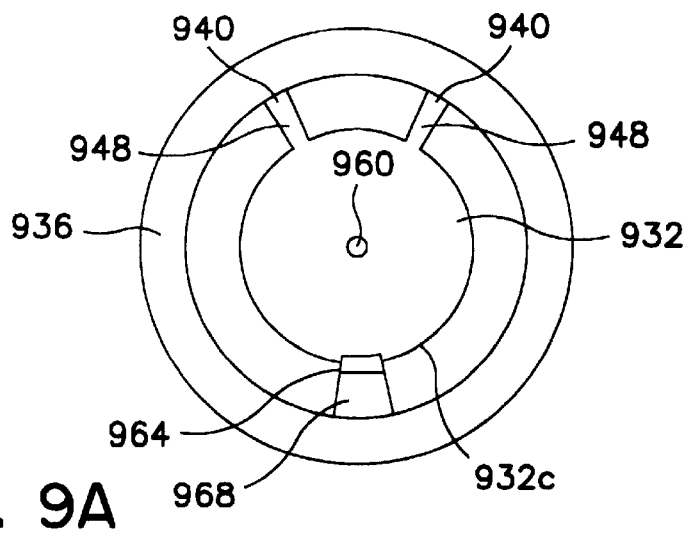
FIG. 9A shows a close-up end view of an alternative embodiment of the valve.

Turning now to FIG. 9A, there is shown a top view of flap valve 932, the rings shown jointly as 936 and associated structure. This flap valve 932 may be used in the embodiments shown. The flap valve 932 is attached to the ring 936 by two arms 948, each forming an attachment point 940. The opposite end 932c of the flap 932 engages a catch 964 or similar locking mechanism that is attached to the ring 936 by an arm 968. The catch 964 effectively locks the flap 932 in a proximal position until the user forcibly advances the catheter in a distal direction, causing the catch to release the flap valve 932.

Figure 9B:
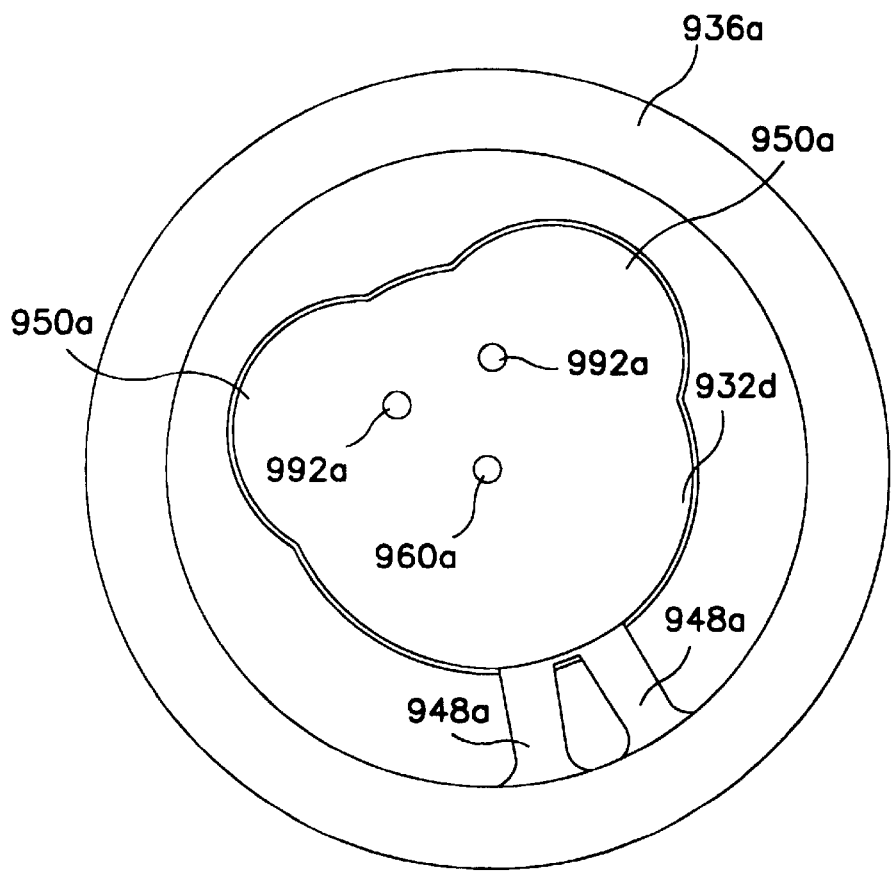
FIG. 9B shows a close-up end view of an alternative embodiment of the valve.

Those skilled in the art will appreciate that numerous modifications could be used to accomplish the principles of the present invention. As an example, a single arm 948 could be used with the flap 932, and multiple catches 964 could be used. Likewise, a single ring could be used rather than the rings 936a to support the flap 932 and the catch 964. Furthermore, as is shown in FIG. 9B, modifications can be made the flap 932d, to provide other benefits. As shown in FIG. 9B, a pair of arms 948a attaches the flap 932d to the ring 936a. As mentioned above, the arms 948a could be configured to bias the flap 932d into the closed position. This flap 932d further comprises at least one protrusion 992a, a pair of protrusions 992a are shown herein, to aid in the retention of mucus and secretions until the catheter enters the cleaning chamber as discussed herein.

The flap 932d is generally circular, but has two rounded projections 950a that extend outwardly and are spaced approximately 90 degrees apart. The projections serve two important purposes. First, even if the generally circular portion of the flap 932d were slightly smaller than the distal opening of the endotracheal tube (not shown), the projections 950a would prevent the flap from entering the endotracheal tube. Second, the projections 950a would cause the flap to align for airflow to continue to the patient without lying flat to cover any passage which might interfere with airflow to or from the patient.

Also shown in FIG. 9B is the aperture 960a that is formed in the generally circular portion of the flap 932d. As shown, the aperture 960a is between about 0.76 mm (0.03 inches) and about 1.02 mm (0.04 inches) in diameter. While shown as being circular or disk-shaped, those skilled in the art will appreciate, in light of the present disclosure, that other shaped apertures could also be used.

Figure 10A:
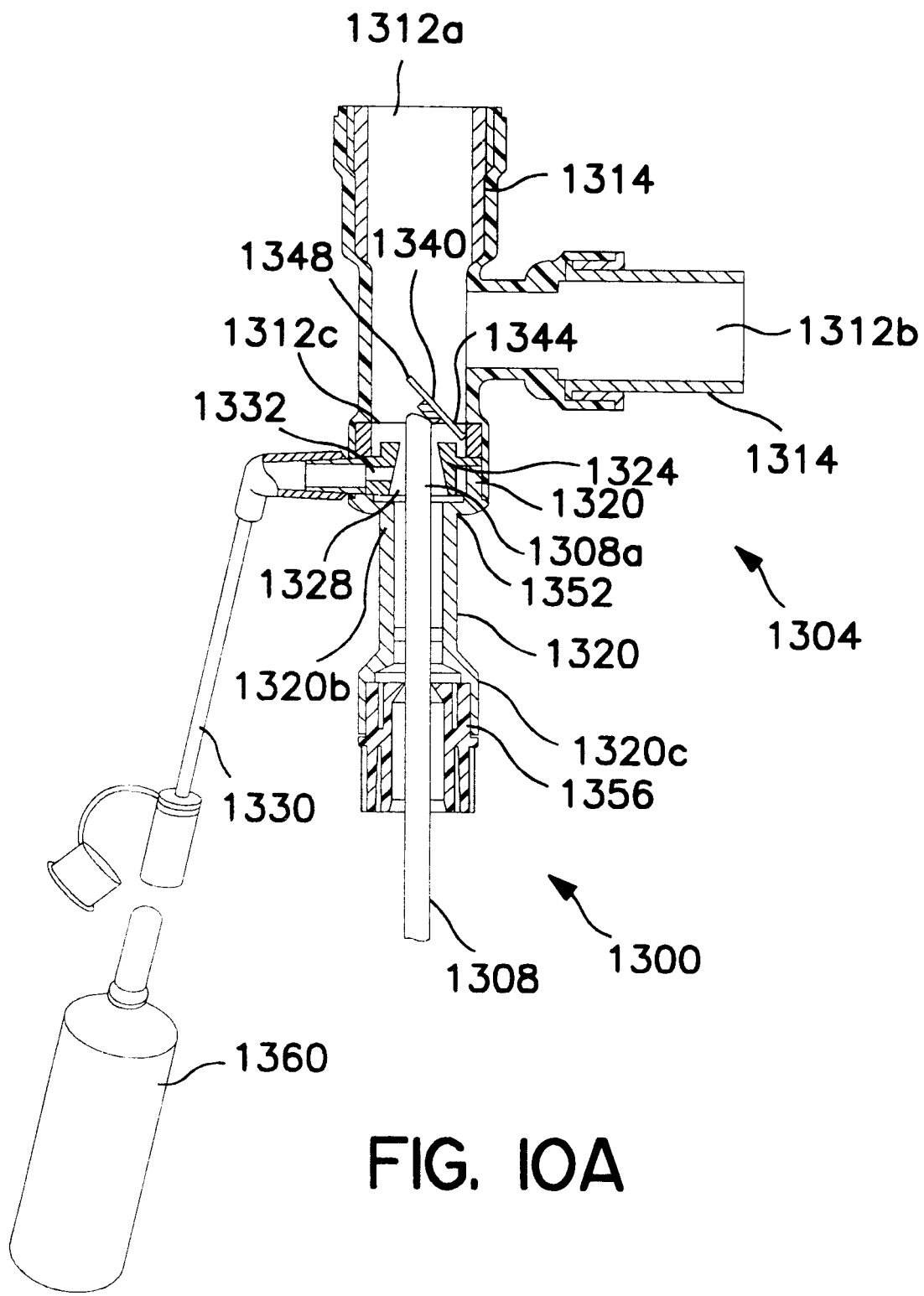
FIG. 10A shows a fragmented, cross-sectional view of an alternate embodiment of an improved endotracheal catheter in which a pair of seals are used to enhance cleaning of the distal end of the catheter tube.

FIG. 10A shows a cross-sectional view of an embodiment of an endotracheal catheter system 1300 that incorporates aspects of the present invention. The endotracheal catheter system 1300 includes a manifold, generally indicated at 1304 which forms a fitting for connecting the endotracheal catheter system 1300 to the artificial airway (i.e. endotracheal tube) of a patient. The endotracheal catheter system 1300 also includes an elongate catheter 1308.

The manifold 1304 includes a first port 1312a, a second port 1312b, and a third port 1312c, The first port 1312a is configured to engage an artificial airway, such as an endotracheal tube. The second port 1312b provides inspiratory and expiratory airflow to and from the patient. Typically, a Y-shaped adapter is attached to the second port 1312b. However, many configurations are used in the clinical setting and those skilled in the art will appreciate the different combinations that are available.

The third port 1312c is disposed opposite the first port 1312a and aligned so that the catheter 1308 can pass through the third port, through the manifold 1304 and through the first port into the artificial airway. As shown in FIG. 10A, the first and second ports 1312a and 1312b may also have swivel structures 1314 to enable the manifold 1304 to swivel with respect to adjoining structures and thereby improve patient comfort.

Connected to the third port 1312c is a coupling or adapter 1320. On the outer surface of the distal end 1320a, the adapter 1320 engages the wall defining the third port 1312c. The inner surface of the adapter 1320 forms a chamber about the distal end 1308a of the catheter 1308. This chamber assists in cleaning the distal end of the catheter in a manner that will be discussed more fully below. Disposed adjacent to the distal end 1320a of the adapter 1320 is a collar 1324 which has a frustoconical bore 1328 extending therethrough. Those skilled in the art will appreciate that the collar 1324 could be formed integrally with the adapter 1320 if desired.

When saline solution is injected through a lavage port 1330 and a side opening 1332 into the frustoconical bore 1328, the collar 1324 helps to channel the saline solution along the catheter 1308, through the first port 1312a and into the artificial airway. The distal end 1324a of frustoconical bore forms an orifice in the distal end of the collar 1324. A flap 1340, supported by a support ring 1344 disposed in the third port 1312c selectively engages the orifice to substantially occlude the orifice when the two are engaged. As with prior embodiments, the flap 1340 preferably has one or more holes 1348 formed therein to allow a small amount of air through the flap valve. Also, like prior embodiments, the flap valve 1340 may be biased in the closed position, or may be drawn into the closed position by suction through the catheter 1308.

Disposed at the opposing, proximal end of the collar 1324 is a wiper seal 1352. Preferably, a narrowed portion 1320b of the adapter 1320 supports the wiper seal 1352. Those skilled in the art, however, will appreciate that other mechanisms for holding the wiper seal 1352 could be used. As the catheter 1308 is withdrawn past the wiper seal 1352, the wiper seal removes major secretions.

From the wiper seal 1352, the adapter 1320 extends proximally and forms a cleaning chamber. Disposed adjacent a proximal end 1320c of the adapter 1320 is a pressure seal 1356. As with the wiper seal 1352, the object of the pressure seal 1356 is to remove secretions from the exterior of the catheter 1308 as it is withdrawn from the artificial airway of the patient. However, the pressure seal 1356 will typically have a smaller diameter opening so that the pressure seal 1356 more closely engages the exterior of the catheter 1308 than the wiper seal 1352.

Figure 10B:
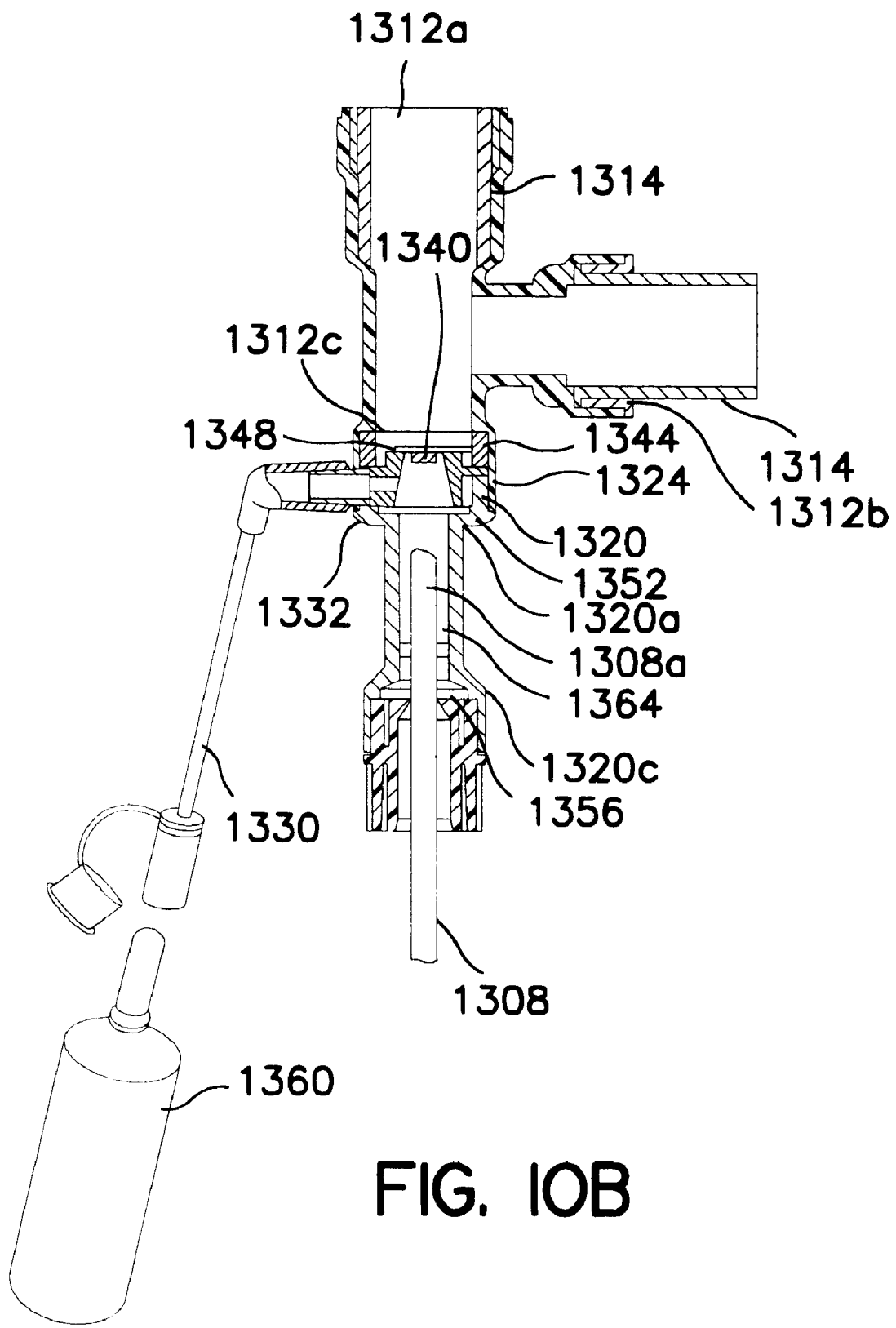
FIG. 10B shows a cross-sectional view similar to that of FIG. 10A, but with the catheter tube pulled back into a proximal position.

Turning now to FIG. 10B, there is shown a side cross-sectional view of the endotracheal catheter assembly 1300 in which the catheter 1308 has been withdrawn through the manifold 1304 into a cleaning position. As the catheter 1308 is withdrawn, the flap 1340 closes—either due to a bias or the suction through the catheter—to occlude the opening in the collar 1324.

As the catheter 1308 is withdrawn proximally out of the collar 1324 and past the wiper seal 1352, the distal end 1308a of the catheter is wiped by the wiper seal 1352 so that most secretions thereon are removed. The secretions that are removed by the wiper seal 1352 are then carried through the catheter 1308.

Once the distal end 1308a of the catheter 1308 has advanced beyond the first wiper seal 1352, a bottle 1360 is attached to the lavage port 1330 and a cleaning liquid (typically saline solution) is supplied through the side opening 1332 in the collar 1324. The cleaning liquid flows around the distal end 1308a of the catheter 1308, indicated by arrow 1364, and cleans those secretions which were not removed by the wiper seal 1352 from the distal end of the catheter. At the same time, the holes 1348 in the flap 1340 allow a small amount of air into the catheter, thereby facilitating removal of the secretions. If desired, a make-up air valve could be disposed on the side of the adapter 1320 to allow the inflow of additional air.

In effect, the seals and valves can be comprised of such synthetic resins as polyurethanes, ethylene vinyl acetate copolymers, polyvinyl chlorides, polysilicones, polyamides, such as nylon, polyethylene, including those of the high density, low density, intermediate density and linear low density variety, ethylene α-lefin copolymers (such as ethylene propylene copolymers), polyesters, polycarbonates, acrylonitrile-butadiene-styrene copolymers, polyether-polyester copolymers, and polyether polyamide copolymers are desirable. Further desirable are low pressure, relatively soft or flexible polymeric materials, such as thermoplastic polymers including thermoplastic elastomers.

Injection molded medical grade synthetic resinous materials are preferable for such internal components. Suitable resins include Pebax® by Atochem North America, Inc., Philadelphia Pa. Most preferred are the Pebax® 33 polyamide/polyether polymers, such as Pebax® 3533 SA 00 polymers. Such polymers may be characterized by a Shore D, ASTM D2240, hardness of about 35, a Shore A, ASTM D2240, hardness of about 85, and a flexural modulus, ASTM D790, of about 19995500 Pa (2,900 PSI), a softening point, ASTM D1525, of approximately 73° C. (165° F.) and a melting point of between about 109° C. (228° F.) and about 154° C. (309° F.). Further preferred is Pebax® 5533 SA 00 polyether block amide polymer characterized by a Shore D, ASTM D2240, hardness of about 55, a flexural modulus, ASTM D790, of about 165480000 Pa (24,000 PSI), a softening point, ASTM D1525, of approximately 144° C. (291° F.). and a melting point of between about 128° C. (262° F.) and about 170° C. (338° F.).

Thermoplastic elastomeric polymers which render excellent results as the internal components for use in the invention further include those sold under the Monprene® name, a trademark of QST, Inc., including Monprene® MP-2870M, having a Shore A hardness, ASTM D2240, of about 70; Santoprene® name, a trademark of Advanced Elastomer Systems, including Santoprene® MP-2870M, having a Shore D hardness, ASTM D2240, of about 40; polyurethane (polyether) elastomers, such as those sold under tlie Pellathane™ name, a trademark of Dow Plastics, including Pellathane® 2363-80AE, having a Shore A hardness, ASTM D2240, of about 85; ethylene vinyl acetate polymer sold under the Elvax® name, a trademark of E.I. du Pont Packaging & Industrial Polymers, including Elvax® 150 (33% vinyl acetate) and Elvax® 360 (25% vinyl acetate), Elvax® 450 (18% vinyl acetate) or Elvax(® 750 (9% vinyl acetate); low density polyethylene polymers, such 3447500 Pa (500 PSI); the low density polyethylenes sold under the Petrothene® trademark by Equistar Chemicals, L.P., such as Petrothene® NA 270-000 low density polyethylene polymer; polyvinyl chlorides commercially available under the Unichem™ trademark by Colorite Plastics Company, such as Unichem™ 7811G-015 polyvinyl chloride polymer, Unichem™ 851G-015 flexible polyvinyl chloride polymer, Unichem™ 6511G-015 flexible polyvinyl chloride polymer; the styrene ethylene butylene styrene block copolymers commercially available under the Kraton™ trademark by Shell Chemical Company, such as the Kraton™ G-7705 styrene ethylene butylene styrene block copolymer; and the density polyethylene polymers commercially available under the Tenite™ trademark by Eastman Chemical Company, such as the Tenite™ 1870A low density polyethylene polymers. Additionally, resins including thermoplastic polyurethane elastomers, thermoplastic elastomers, polyether block amides, silicones and/or rubbers, provide the preferred resilient elasticity in each seal and/or valve for efficient cleaning.

By use of these various configurations, the cleaning of the distal end of a catheter may be enhanced while minimizing or eliminating the air drawn from the ventilation circuit of the patient. Those skilled in the art will appreciate modifications that can be made without departing scope and spirit of the present invention. The appended claims are intended to cover such modifications.

What is claimed is:

1. A respiratory suction system comprising:
   an elongate catheter;
   a manifold having a passageway into which the catheter may be advanced;
   at least one resilient seal disposed within the manifold, a distal surface of the seal having a cross area sufficient to wipe the catheter when the catheter is retracted from the manifold; and
   at least one pressure seal disposed proximal to the resilient seal within the manifold having a cross area sufficient to engage the catheter and maintain pressure in the manifold.

2. The respiratory suction system of claim 1, further comprising a valve disposed within the manifold distal to the resilient seal to selectively occlude the retracted catheter from the manifold.

3. The respiratory suction system of claim 2, wherein the valve is moveable between an open and a closed position.

4. The respiratory suction system of claim 3, wherein the valve comprises a flap that is pivot able between the open and closed position.

5. The respiratory suction system of claim 2, wherein the valve comprises a collar having a bore therethrough and a flap configured for selectively engaging the collar to at least partially cover the bore.

6. The respiratory suction system of claim 2, wherein the valve comprises a ring disposed within the manifold and a flap pivotably attached to the ring.

7. The respiratory suction system of claim 2, further comprising a cleaning chamber defined by the valve and the pressure seal.

8. The respiratory suction system of claim 7, further comprising a lavage port having an opening disposed in fluid communication with the cleaning chamber which is disposed distally of the pressure seal.

9. The respiratory suction system of claim 1, wherein the resilient seal is a cylindrical disk.

10. The respiratory suction system of claim 9, wherein the cylindrical disk has an aperture formed therein.

11. The respiratory suction system of claim 9, wherein the valve has at least one protrusion extending from its proximal planar surface.

12. The respiratory suction system of claim 1, further comprising a lavage port distal of the pressure seal.

13. The respiratory suction system of claim 1, wherein the catheter is encased within a collapsible sheath.

14. The respiratory suction system of claim 1, the catheter further comprising a distal end, wherein the at least one resilient seal contacts the distal end of the catheter when the catheter is retracted from the manifold.

15. The respiratory suction system of claim 14, wherein the at least one resilient seal is a wiper seal.

16. A respiratory suction system comprising:
   an elongate catheter;
   a manifold having a passageway into which the catheter may be advanced;
   at least one resilient seal disposed within the manifold, a distal surface of the seal having a cross area sufficient to wipe the catheter when the catheter is retracted from the manifold;
   at least one pressure seal disposed proximal to the resilient seal within the manifold having a cross area sufficient to engage the catheter and maintain pressure in the manifold; and
   a valve disposed within the manifold distal to the resilient seal to selectively occlude the retracted catheter from the manifold.

17. The respiratory suction system of claim 16, wherein the valve comprises a flap that is pivotable between the open and closed position.

18. The respiratory suction system of claim 17, wherein the flap has at least one protrusion extending from its proximal planar surface.

19. The respiratory suction system of claim 16, wherein the valve and/or seal is composed of a medical grade synthetic resin selected from polyurethanes, ethylene vinyl acetate copolymers, polyvinyl chlorides, polyamide/polyethers, polysilicones, polyamides, polyethylene, ethylene α-olefin copolymers, polyesters, polycarbonates, acrylonitrile-butadiene-styrene copolymers and polyether polyester copolymers.

20. The respiratory suction system of claim 19, wherein the valve and/or seal is composed of a polyether block amide.

21. The respiratory suction system of claim 16, the catheter further comprising a distal end, wherein the at least one resilient seal contacts the distal end of the catheter when the catheter is retracted from the manifold.

22. The respiratory suction system of claim 21, wherein the at least one resilient seal is a wiper seal.

23. A respiratory suction system comprising:
   an elongate catheter having a distal end;
   a manifold having a passageway into which the catheter may be advanced;
   at least one resilient seal disposed within the manifold, a distal surface of the seal having a cross area sufficient to wipe the catheter when the catheter is retracted from the manifold; and
   a valve disposed within the manifold distal to the resilient seal to selectively restrict the retracted catheter from the manifold, wherein movement of the distal end of the catheter distally through the valve will move the valve to an open position.

24. The respiratory suction claim 23, further comprising at least one pressure seal disposed proximal to the resilient seal within the manifold having a cross area sufficient to engage the catheter and maintain pressure in the manifold.

25. The respiratory suction system of claim 23, herein the at least one resilient seal contacts the distal end of the catheter when the catheter is retracted from the manifold.

26. The respiratory suction system of claim 25, wherein the at least one resilient seal is a wiper seal.

* * * * *